US012797008B2

(12) United States Patent
Russomanno et al.

(10) Patent No.: US 12,797,008 B2
(45) Date of Patent: Nov. 17, 2026

(54) MULTI-LAYER HEADGEAR SYSTEM

(71) Applicant: OpenBCI, Inc., Brooklyn, NY (US)

(72) Inventors: Conor Russomanno, Brooklyn, NY (US); Shi Gang Yuan, Middle Island, NY (US); Joseph Artuso, Brooklyn, NY (US); Blake Michael Larkin, Brooklyn, NY (US); Robert Shusko, Merrick, NY (US)

(73) Assignee: OpenBCI, Inc., Brooklyn, NY (US)

( * ) Notice: Subject to any disclaimer, the term of this patent is extended or adjusted under 35 U.S.C. 154(b) by 66 days.

(21) Appl. No.: 18/745,950

(22) Filed: Jun. 17, 2024

(65) Prior Publication Data

US 2024/0335166 A1 Oct. 10, 2024

Related U.S. Application Data

(63) Continuation of application No. 18/324,667, filed on May 26, 2023, now Pat. No. 12,013,724.

(60) Provisional application No. 63/346,348, filed on May 27, 2022.

(51) Int. Cl.
*A61B 5/00* (2006.01)
*G06F 1/16* (2006.01)
*A61B 5/0205* (2006.01)

(52) U.S. Cl.
CPC .......... *A61B 5/6803* (2013.01); *A61B 5/6817* (2013.01); *G06F 1/163* (2013.01); *A61B 5/02055* (2013.01)

(58) Field of Classification Search
CPC .... A61B 5/6803; A61B 5/02427; G06F 1/163
USPC .............................................................. 2/422
See application file for complete search history.

(56) References Cited

U.S. PATENT DOCUMENTS 4,967,038 A 10/1990 Gevins
11,207,490 B1 * 12/2021 Fried ......................... A61F 9/04
12,013,724 B1 * 6/2024 Russomanno ..... A61B 5/02438
2015/0148681 A1 * 5/2015 Abreu .................. A61B 5/6821
600/474

(Continued)

FOREIGN PATENT DOCUMENTS

WO WO-2022221907 A1 * 10/2022 .............. G06F 3/011
WO WO-2024011291 A1 * 1/2024 ......... G02B 27/0176

(Continued)

OTHER PUBLICATIONS

NOK Corporation "Business Report for the 114th Term" 30 pages, 2020.

(Continued)

*Primary Examiner* — Tajash D Patel
(74) *Attorney, Agent, or Firm* — Esplin & Associates, PC

(57) ABSTRACT

A multi-layer headgear system may comprise one or more of a head-mounted display adapter plate, a headgear frame, a sensor-engagement assembly, and/or other components. A first side of the head-mounted display adapter plate may be configured to be attached to a head-mounted display. A second side of the head-mounted display adapter plate may be configured to be attached to a first side of the headgear frame. A first side of the sensor-engagement assembly may be configured to be attached to a second side of the headgear frame. The sensor-engagement assembly may be configured to position one or more sensors with respect to a face.

20 Claims, 27 Drawing Sheets

350

(56) References Cited

U.S. PATENT DOCUMENTS

| | | | | |
|---|---|---|---|---|
| 2015/0182165 | A1 | 7/2015 | Miller | |
| 2016/0143554 | A1 | 5/2016 | Lim | |
| 2016/0216760 | A1* | 7/2016 | Trutna | G06F 3/012 |
| 2017/0143228 | A1 | 5/2017 | Leuthardt, Jr. | |
| 2017/0296121 | A1 | 10/2017 | Dar | |
| 2020/0029881 | A1 | 1/2020 | Flood | |
| 2021/0345927 | A1 | 11/2021 | Kitazoe | |
| 2023/0263447 | A1 | 8/2023 | Vrijens | |
| 2024/0180468 | A1 | 6/2024 | Russomanno | |
| 2025/0110556 | A1* | 4/2025 | Zhang | G06F 3/017 |
| 2026/0076603 | A1 | 3/2026 | Russomanno | |
| 2026/0118675 | A1* | 4/2026 | Sumanaweera | G02B 27/0172 |

FOREIGN PATENT DOCUMENTS

| | | | | |
|---|---|---|---|---|
| WO | WO-2024221056 | A1 * | 10/2024 | G02B 27/0179 |
| WO | WO-2026090657 | A1 * | 5/2026 | A61N 1/0408 |

OTHER PUBLICATIONS

Orbital Research Inc. “Orbital’s Portfolio of Dry Electrodes” 1 page, 2020.

* cited by examiner

350

1010

MULTI-LAYER HEADGEAR SYSTEM

CROSS-REFERENCE TO RELATED APPLICATIONS

The present application claims the benefit of U.S. Provisional Application No. 63/346,348, entitled "SYSTEM, METHOD, COMPONENT, AND INTERFACE OF HEAD-MOUNTED DISPLAY (HMD)," which was filed on: May 27, 2022, the entirety of which is hereby incorporated herein by reference.

FIELD

The present disclosure relates generally to the field of multi-layer headgears for positioning sensors with respect to a face.

BACKGROUND

Sensors may be mounted on a headgear to collect biometric data from a person's head/face. Due to the variability in shapes and sizes of people's heads/faces, static placement of the sensors on the headgear may result in improper positioning of the sensors when the headgear is worn by a person.

SUMMARY

This disclosure relates to a multi-layer headgear system. The multi-layer headgear system may comprise one or more of a head-mounted display adapter plate, a headgear frame, a sensor-engagement assembly, and/or other components. A first side of the head-mounted display adapter plate may be configured to be attached to a head-mounted display. A second side of the head-mounted display adapter plate may be configured to be attached to a first side of the headgear frame. A first side of the sensor-engagement assembly may be configured to be attached to a second side of the headgear frame. The sensor-engagement assembly may be configured to position one or more sensors with respect to a face.

In some implementations, the first side of the head-mounted display adapter plate may be shaped to mate with a type of the head-mounted display. Different types of the head-mounted display adapter plate may enable different types of the head-mounted display to be used with the sensor-engagement assembly. The head-mounted display adapter plate may convert the shape of the head-mounted display for mating with the headgear frame.

In some implementations, the one or more sensors of the sensor-engagement assembly may be configured to acquire one or more electrical signals and/or one or more optical signals from the face. The sensor(s) may be configured to acquire the electrical signal(s) and/or the optical signal(s) from the face with or without the first side of the head-mounted display adapter plate attached to the head-mounted display.

In some implementations, the sensor-engagement assembly may include a face liner. The headgear frame may be configured to flex the face liner onto the face and conform the face liner to a shape of the face. The headgear frame may include a rigid structure, and the face liner may include a flexible structure. The flexing of the face liner onto the face may be controlled via movement of screws on the headgear frame or change in positioning of the face liner with respect to the headgear frame.

In some implementations, the second side of the head-mounted display adapter plate may be configured to be removably attached to the first side of the headgear frame. In some implementations, the second side of the head-mounted display adapter plate may be configured to be rotatably attached to the first side of the headgear frame. In some implementations, the second side of the head-mounted display adapter plate may be configured to be locked with the first side of the headgear frame.

These and other objects, features, and characteristics of the system and/or method disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a," "an," and "the" include plural referents unless the context clearly dictates otherwise.

BRIEF DESCRIPTION OF THE DRAWINGS

FIGS. 10A, 101B, and 10C illustrate example multi-layer headgear systems.

DETAILED DESCRIPTION

The present disclosure relates to a multi-layer headgear system. The multi-layer headgear system may comprise one or more of a head-mounted display adapter plate, a headgear frame, a sensor-engagement assembly, and/or other components. A first side of the head-mounted display adapter plate may be configured to be attached to a head-mounted display. A second side of the head-mounted display adapter plate may be configured to be attached to a first side of the headgear frame. A first side of the sensor-engagement assembly may be configured to be attached to a second side of the headgear frame. The sensor-engagement assembly may be configured to position one or more sensors with respect to a face.

Biometric data of a person may be obtained via use of one or more sensors positioned with respect to the person's face. The sensor(s) may be mounted on a headgear to be worn by the person. However, static positioning of the sensor(s) may result in improper positioning of the sensor(s) due to the variability in shapes and sizes of people's heads/faces. Building differently configured headgears that include sensors and head-mounted displays for heads/faces of different shapes and sizes may be costly and impractical.

The present disclosure provides a generalized and flexible multi-layer headgear system to overcome the above and other deficiencies. The multi-layer headgear system of the present disclosure utilizes multiple layers to combine a head-mounted display with one or more sensors, enabling the user to use the head-mounted display while positioning the sensor(s) for biometric data measurement. The multi-layer headgear system enables positioning of the sensor(s) without obstruction from the head-mounted device. The multi-layer headgear system enables the user to move, remove, and/or replace the head-mounted display. The layer design of the multi-layer headgear system enables different components and/or layers of the multi-layer headgear system to be fixed and/or replaced without having to replace the entire system. For example, the layer of the multi-layer headgear system that touches the user's face may wear out over time. Rather than having to replace the entire system, the worn-out layer may be fixed and/or replaced. The worn-out layer may be removed from the system to facilitate repair.

The multi-layer headgear system may comprise one or more of a head-mounted display adapter plate, a headgear frame, a sensor-engagement assembly, and/or other components. The multi-layer headgear system may be combined with a head-mounted display and worn by a person to position one or more sensors with respect to the person's face.

Figure 1:
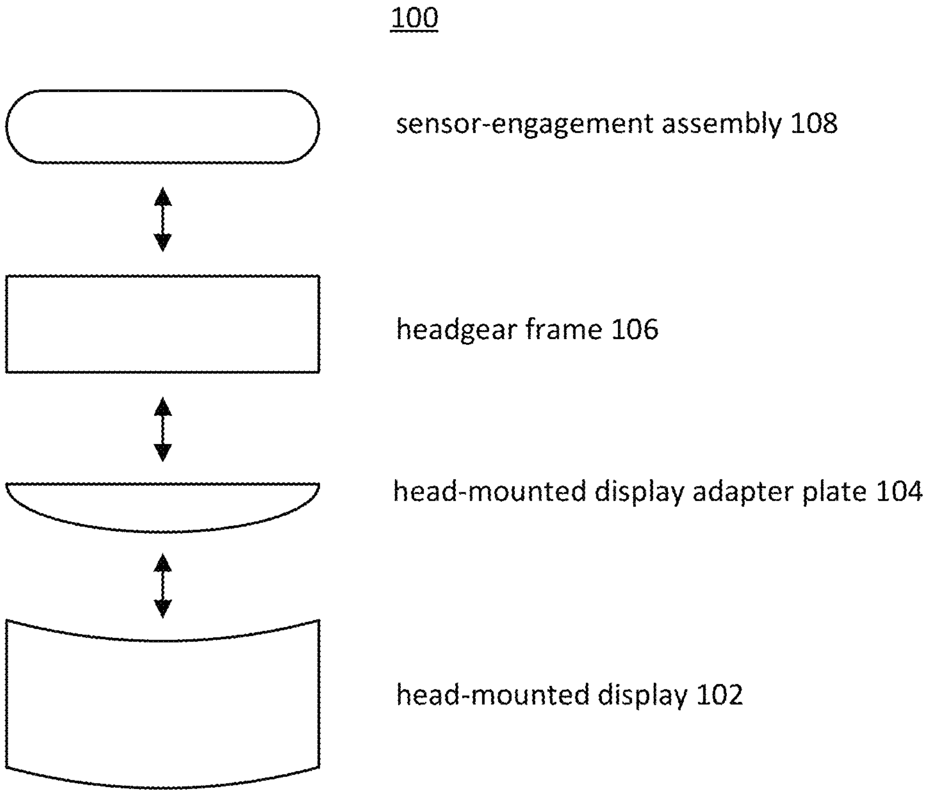
FIG. 1 illustrates an example multi-layer headgear system.

FIG. 1 illustrates an example multi-layer headgear system 100. The multi-layer headgear system 100 may comprise a head-mounted display 102, a head-mounted display adapter plate 104, a headgear frame 106, a sensor-engagement assembly 108, and/or other components. Other configurations of a multi-layer headgear system are contemplated.

The head-mounted display 102 may refer to an electronic display device that is worn on the head or as part of a headgear. A headgear may refer to a covering or protective device for the head, such as a helmet. The head-mounted display 102 may be a commercially available head-mounted display or a non-commercially available head-mounted display. In some implementations, the head-mounted display 102 may be modified for use in/with the multi-layer headgear system 100. For example, one or more head straps of the head-mounted display 102 may be removed. As another example, one or more parts of the head-mounted display 102 on the face side of the head-mounted display 102, such as foam or inner-shell/housing on the face-side, may be removed.

The head-mounted display adapter plate 104 may refer to a mechanical device/component that enables the head-mounted display 102 to be combined into/with the multi-layer headgear system 100. The head-mounted display adapter plate 104 may refer to a mechanical device/component that converts one or more physical attributes/characteristics of the head-mounted display 102 into one or more physical attributes/characteristics that may be combined/compatible with the headgear frame 106. The head-mounted display adapter plate 104 may be made of metallic material, polymeric material, and/or other types of material.

One or more sides of the head-mounted display adapter plate 104 may be configured to be attached to the head-mounted display 102, while one or more other sides of the head-mounted display adapter plate 104 may be configured to be attached to the headgear frame 106. For example, the frontside of the head-mounted display adapter plate 104 may be configured to be attached to the backside of the head-mounted display 102, and the backside of the head-mounted display adapter plate 104 may be configured to be attached to the frontside of the headgear frame 106.

The head-mounted display adapter plate 104 being configured to be attached to another device/component (e.g., the head-mounted display 102, the headgear frame 106) may include the head-mounted display adapter plate 104 having physical attributes/characteristics that enables the head-mounted display adapter plate 104 to be attached to (e.g., joined to, fastened to, combined with) the other device/component. For example, part(s) and/or surface(s) of the frontside of the head-mounted display adapter plate 104 may be shaped to mate with part(s) and/or surface(s) of the backside of the head-mounted display 104. Part(s) and/or surface(s) of backside of the head-mounted display adapter plate 104 may be shaped to mate with part(s) and/or surface (s) of the frontside of the headgear frame 106. The head-mounted display adapter plate 104 may be attached to another device/component using screws, fasteners, clips, magnets, fittings, snaps, and/or other attachment techniques/tools.

In some implementations, one or more sides of the head-mounted display adapter plate 104 may be shaped to mate with a particular type of head-mounted display. For example, part(s) and/or surface(s) of the frontside of the head-mounted display adapter plate 104 may be shaped to mate with a particular type of head-mounted display. The head-mounted display adapter plate 104 may convert the shape of the head-mounted display 102 for mating with the headgear frame 106. For example, the shape of the Backside of the head-mounted display 102 may be incompatible with the headgear frame 106. Different types of head-mounted displays may have differently shaped backsides.

Rather than providing differently shaped headgear frame 106 for different types of head-mounted displays, differently shaped head-mounted display adapter plate 104 may be provided for different types of head-mounted displays. Different types of head-mounted display adapter plate 104 may enable different types of the head-mounted display to be used with the sensor-engagement assembly 108. Use of differently shaped head-mounted display adapter plate 104 enables different types of head-mounted displays to be combined with the headgear frame 106 without changing the design of the headgear frame 106.

The headgear frame 106 may refer to a mechanical device/component that provides the main structure of the multi-layer headgear system 100. The headgear frame 106 may refer to a mechanical device/component that provides structural support and proper spacing for other components of the multi-layer headgear system 100. The headgear frame 106 may provide the skeleton frame/chassis of the multi-layer headgear system 100. The headgear frame 106 may be made of metallic material, polymeric material, and/or other types of material.

The headgear frame 106 may be configured to be attached to the head-mounted display adapter plate 104 and the sensor-engagement assembly 108. One or more sides of the headgear frame 106 may be configured to be attached to the head-mounted display adapter plate 104, while one or more other sides of the headgear frame 106 may be configured to be attached to the sensor-engagement assembly 108. For example, the frontside of the headgear frame 106 may be configured to be attached to the backside of the head-mounted display adapter plate 104, and the backside of the headgear frame 106 may be configured to be attached to the frontside of the sensor-engagement assembly 108. The headgear frame 106 being configured to be attached to another device/component (e.g., the head-mounted display adapter plate 104, the sensor-engagement assembly 108) may include the headgear frame 106 having physical attributes/characteristics that enables the headgear frame 106 to be attached to (e.g., joined to, fastened to, combined with) the other device/component. The headgear frame 106 may be attached to another device/component using screws, fasteners, clips, magnets, fittings, snaps, and/or other attachment techniques/tools.

The sensor-engagement assembly 108 may refer to a mechanical device/component that provides sensor positioning with respect to a face. The sensor-engagement assembly 108 may provide the shape/contour needed to properly position one or more sensors with respect to the face. The sensor engagement assembly 108 may refer to a group/collection of parts that enable sensor(s) to be positioned at various locations around the face. For example, the sensor engagement assembly 108 may include foam pad(s)/substrate(s), sensor(s), flexible printed circuit board(s), and/or other components. The sensor(s) and/or other electronic component(s) may be embedded within the foam pad(s)/substrate(s). In some implementations, the foam pad(s)/substrate(s) may include different types of layers/foams. For example, the foam pad(s)/substrate(s) may include multiple layers of different types of foam and an electrical layer to provide conformance, comfort, data collection, and/or aesthetics. The sensor engagement assembly 108 may be made of metallic material, polymeric material, and/or other types of material.

In some implementations, the sensor engagement assembly 108 may be flexible. The sensor engagement assembly 108 may be flexed to provide conformity to a person's face. The flexibility of the sensor engagement assembly 108 may allow the sensor engagement assembly 108 to fit a wide range of face shapes and/or sizes. In some implementations, differently shaped sensor engagement assembly 108 may be provided for different shapes and/or sizes of faces. Use of differently shaped sensor engagement assembly 108 enables the multi-layer headgear system 100 to be used for different faces. For example, a "one-size fits all" sensor engagement assembly 108 may be used for faces of different shapes and/or sizes. As another example, a sensor engagement assembly 108 custom-built for a specific face and/or a specific type of face may be used.

In some implementations, the foam pad(s)/substrate(s) may be attached to different parts of the sensor engagement assembly 108 to enable sensor placement customization. For example, the foam pad(s)/substrate(s) may be placed at different locations of the sensor engagement assembly 108 so that the sensors' position with respect to the face may be varied when the multi-layer headgear system 100/the headgear frame 106 is worn by the person.

The sensor-engagement assembly 108 may be configured to be attached to the headgear frame 106. One or more sides of the sensor-engagement assembly 108 may be configured to be attached to the headgear frame 106. For example, the frontside of the sensor-engagement assembly 108 may be configured to be attached to the backside of the headgear frame 106. The sensor-engagement assembly 108 being configured to be attached to another device/component (e.g., the headgear frame 106) may include the sensor-engagement assembly 108 having physical attributes/characteristics that enables the sensor-engagement assembly 108 to be attached to (e.g., joined to, fastened to, combined with) the other device/component. The sensor-engagement assembly 108 may be attached to another device/component using screws, fasteners, clips, magnets, fittings, snaps, and/or other attachment techniques/tools.

The sensor-engagement assembly 108 may be configured to position one or more sensors with respect to a face. When the multi-layer headgear system 100/the headgear frame 106 is worn by a person, the sensor(s) of the sensor-engagement assembly 108 may be positioned relative to the person's face so that the sensor(s) are able to acquire biometric data, such as the biometric characteristics, from the person's face. In some implementations, positioning of the sensor(s) with respect to the person's face may include positioning of the sensor(s) with respect to the person's head. The sensor(s) may be positioned to acquire biometric data from one or more parts of the person's head, such as the brain and/or the face (e.g., the whole face; part of the face, such as the eyes).

Biometric data of a person may refer to data/information relating to physical and/or behavioral characteristics of the person. Biometric data of a person may include physiological data of the person. Physiological data may refer to data/information about a person's bodily functions, such as heart rate, skin conductance, skin temperature, cortisol level, palmar sweat, and eye tracking. The biometric characteristics of a person may include physical and/or behavioral characteristics of the person. The biometric characteristics of a person may include physiological characteristics of the person. Other types of biometric data are contemplated.

The sensor(s) of the sensor-engagement assembly 108 may be configured to acquire one or more electrical signals, one or more optical signals, and/or other signals from the face. The sensor(s) of the sensor-engagement assembly 108 may be configured to acquire one or more electrical signals, one or more optical signals, and/or other signals from the head. The sensor(s) of the sensor-engagement assembly 108 may be configured to make measurements of one or more biometric characteristics from the person's face/head. The biometric characteristic(s) may be measured from the person's body (e.g., from the skin, blood flow, muscles) and/or from materials on the person's body (e.g., sweat on the skin). The sensor(s) of the sensor-engagement assembly 108 may output signals that convey, reflect, and/or otherwise indicate the measured biometric characteristic(s). The sensor(s) may include one or more electrodes. The sensor(s) of the sensor-engagement assembly 108 may be configured to acquire the electrical signal(s) and/or the optical signal(s) from the face/head and/or make measurements of the biometric characteristic(s) from the person's face/head with or without a side of the head-mounted display adapter plate 104 attached to the head-mounted display 102. The sensor(s) of the sensor-engagement assembly 108 may be configured to acquire the electrical signal(s) and/or the optical signal(s) and/or make measurements with or without attachment of the head-mounted display 102.

One or more types of sensors may be attached to the sensor-engagement assembly 108. Example types of sensors that may be attached to the sensor-engagement assembly 108 include photoplethysmography (PPG) sensor, electroencephalography (EEG) sensor, electromyography (EMG) sensor, electrodermal activity (EDA) sensor, electrooculogram (EOG) sensor, functional near-infrared spectroscopy (fNIRS) sensor, motion sensor (e.g., accelerometer, inertial measurement unit, gyroscope), image sensor (e.g., camera), sound sensor (e.g., microphone), and/or temperature sensor. Other types of sensors may be attached to the sensor-engagement assembly 108. The types of sensors that are attached to the sensor-engagement assembly 108 and/or the location of sensor attachment on the sensor-engagement assembly 108 may be changed.

In some implementations, the sensor-engagement assembly 108 may include a face liner. The face liner may refer to a mechanical device/component of the sensor-engagement assembly 108 that provides shape/contour needed to properly position one or more sensors with respect to the face. The face liner may be made of flexible material, such as polymeric material and/or other types of flexible material. In some implementations, the headgear frame 106 may include a rigid structure, and the face liner may include a flexible structure.

The headgear frame 106 may be configured to flex the face liner onto the face and conform the face liner to the shape of the face. For example, the headgear frame 106 may include mechanisms to push in and/or pull apart the facer liner to flex the face liner. For instance, the flexing of the face liner onto the face may be controlled via movement of screws on the headgear frame. The screws may be moved to apply compressive/mechanical pressure on the face liner. The screws may be moved to flex the face liner onto the face. For example, the screws may be moved to pinch the face liner onto the face.

As another example, the headgear frame 106 may include mechanisms to change the positioning of the face liner with respect to the headgear frame 106. Change in the positioning of the face liner with respect to the headgear frame 106 may include the face liner being moved closer to or away from the headgear frame 106. For example, the headgear frame 106 may include one or more mechanisms that allows the user to pull the face liner away from the headgear frame 106 and squeeze the face liner, along with the sensors/the sensor-engagement assembly 108 attached to the face liner, onto the face.

As the face liner is flexed onto the face, the flexibility of the face liner may enable the face liner to match the shape of the face and position the sensor(s)/the sensor-engagement assembly 108 next/adjacent to the face. Flexing of the face liner may allow the sensor(s) to be ergonomically positioned with respect to the face. Use of other mechanisms to flex the face liner is contemplated.

Figure 2A:
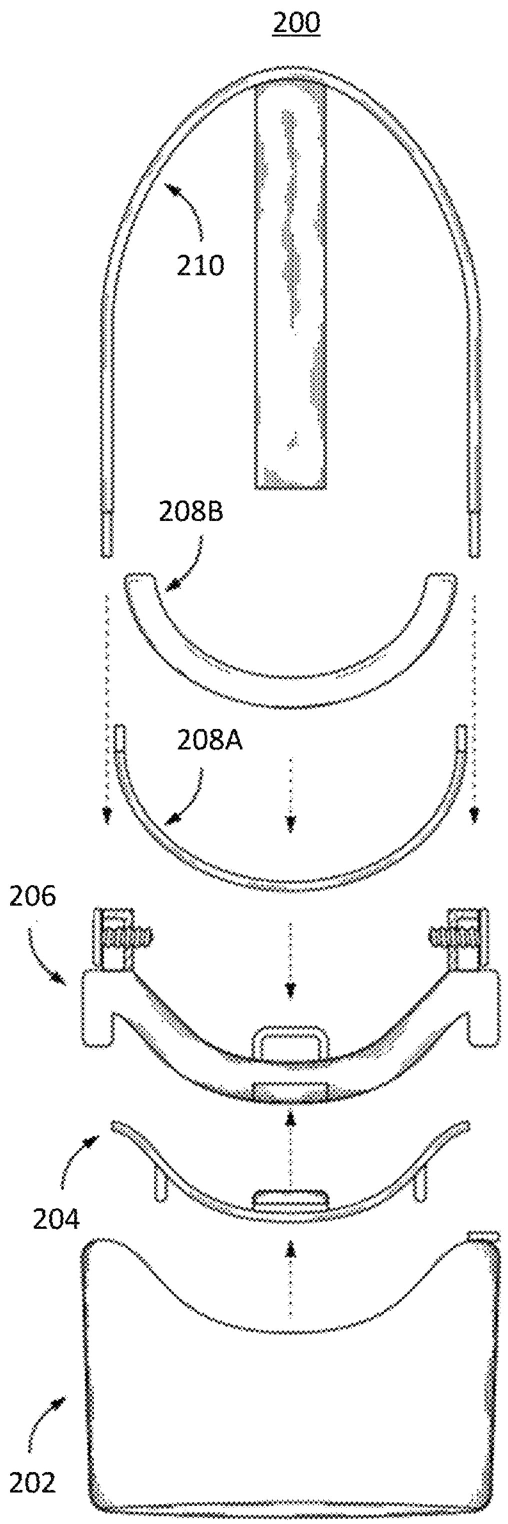
FIGS. 2A and 2B illustrate example multi-layer headgear systems.

FIG. 2A illustrates an example multi-layer headgear system 200. The multi-layer headgear system 200 may include a head-mounted display 202, a head-mounted display adapter plate 204, a headgear frame 206, a sensor-engagement assembly (which includes a face liner 208A and a foam pad/substrate 208B), a head strap 210, and/or other components. The foam pad/substrate 208B may include one or more sensors. The frontside of the head-mounted display adapter plate 204 may be configured to be attached to the backside of the head-mounted display 202. The backside of the head-mounted display adapter plate 204 may be configured to be attached to the frontside of the headgear frame 206. The face liner 208A may be configured to be attached to the headgear frame 206. The movement of the screws on the headgear frame 206 may control flexing of the face liner 208A. The foam pad/substrate 208B may be configured to be attached to the face liner 208A.

When the multi-layer headgear system 200 is assembled and worn by a person, the foam pad/substrate 208B may be configured to position the sensor(s) with respect to the person's face. The head strap 210 may be used to hold the multi-layer headgear system 200 on the person's head. The head strap 210 may go around the side, back, and/or top of the person's head. One or more foam pads/substrates with sensors may be attached to the head strap 210 to enable acquisition of biometric data from other parts of the head. For example, EEG and/or fNIRS sensors may be included within the foam pads/substrates to acquire EEG and/or fNIRS data from the scalp. The head strap 210 may include one or more weights to counterbalance the weight of the head-mounted display 202. For example, the head strap 210 may include weights added to the back, near a strap adjuster, to counterbalance the weight of the head-mounted display 202.

Figure 2B:
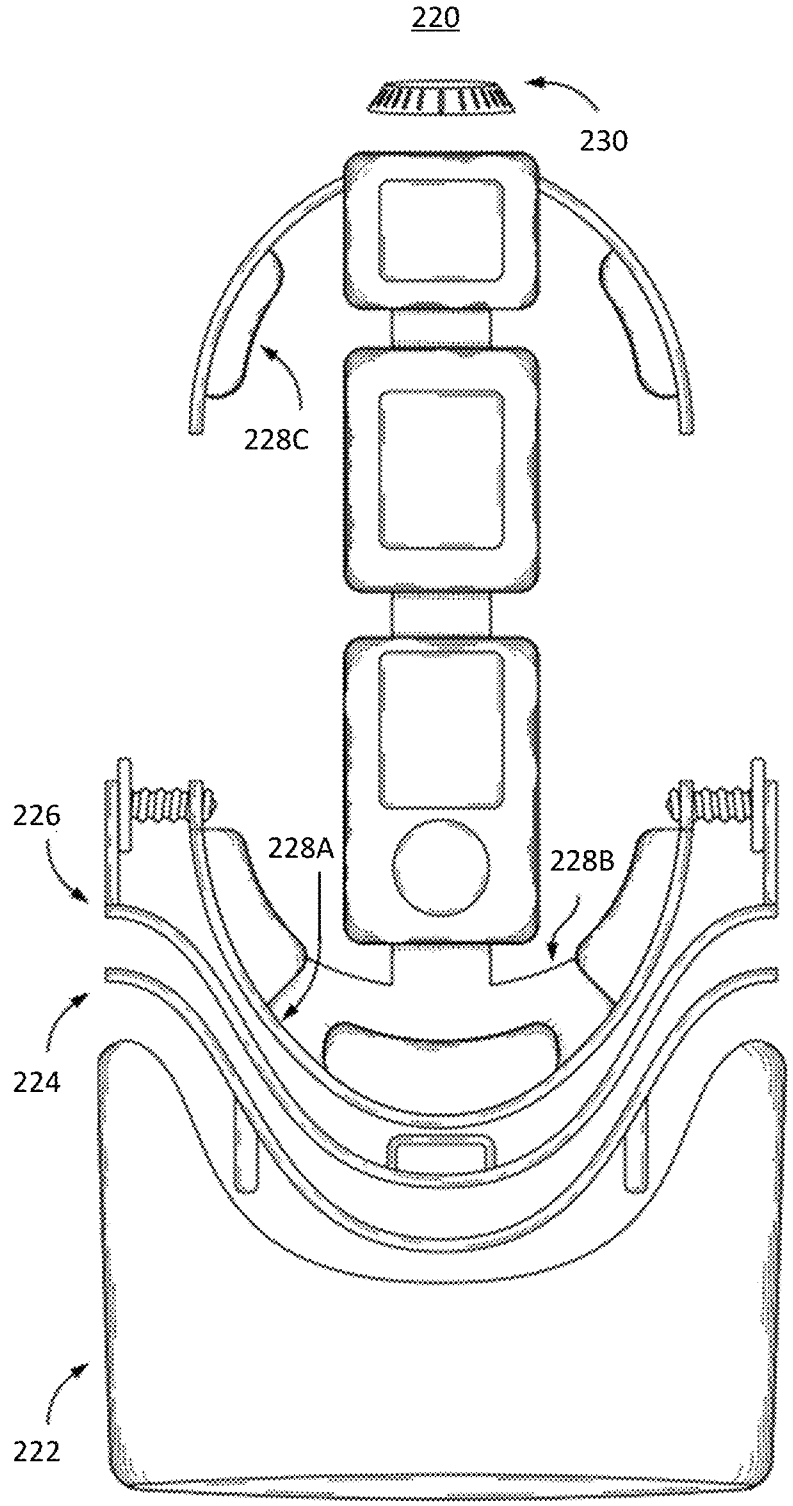

FIG. 2B illustrates an example multi-layer headgear system 220. The multi-layer headgear system 220 may include a head-mounted display 222, a head-mounted display adapter plate 224, a headgear frame 226, a sensor-engagement assembly (which includes a face liner 228A, three foam pads/substrates 228B attached to the face liner 228A, and two foam pads/substrates 228C attached to the back of the headgear frame 226/head strap), a strap adjuster 230 (e.g., tightening wheel), and/or other components. The foam pads/substrates 228B, 228C may include one or more sensors. The frontside of the head-mounted display adapter plate 224 may be configured to be attached to the backside of the head-mounted display 222. The backside of the head-mounted display adapter plate 224 may be configured to be attached to the frontside of the headgear frame 226. The face liner 228A may be configured to be attached to the headgear frame 226. The movement of the screws on the headgear frame 226 may control flexing of the face liner 228A. The movement of the screws on the headgear frame 226 may push in or out the ends of the face liner 228A to flex the face liner 228A. The foam pads/substrates 228B may be configured to be attached to the face liner 228A. The foam pads/substrates 228C may be configured to be attached to the back of the headgear frame 226/head strap.

When the multi-layer headgear system 220 is assembled and worn by a person, the foam pads/substrates 228B, 228C may be configured to position the sensor(s) with respect to the person's face and/or head. The multi-layer headgear system 220 may include a head strap that goes over, around, and/or behind the person's head. The head strap may include foam pads/substrates with sensors. The head strap may be tightened/loosened via the strap adjuster 230. The multi-layer headgear system 220 may include a single system of cables routed throughout that is controlled via the strap adjuster 230. For example, the strap adjuster 230 may be used to control the fit of multiple layers, pads, sensors, and/or other components of the multi-layer headgear system 220.

While FIG. 2B shows screws attached to the face liner 228A, this is merely as an example and is not meant to be limiting. In some implementations, the screws that control flexing of the face liner may touch the face liner without being attached to the face liner. For example, the ends of the screws may contact the face liner and push the face liner in without being attached to the face liner. While FIGS. 2A and 2B show screws to control flexing of the face liner, this is merely as an example and is not meant to be limiting. Use of other mechanisms to flex the face liner is contemplated.

Figure 2C:
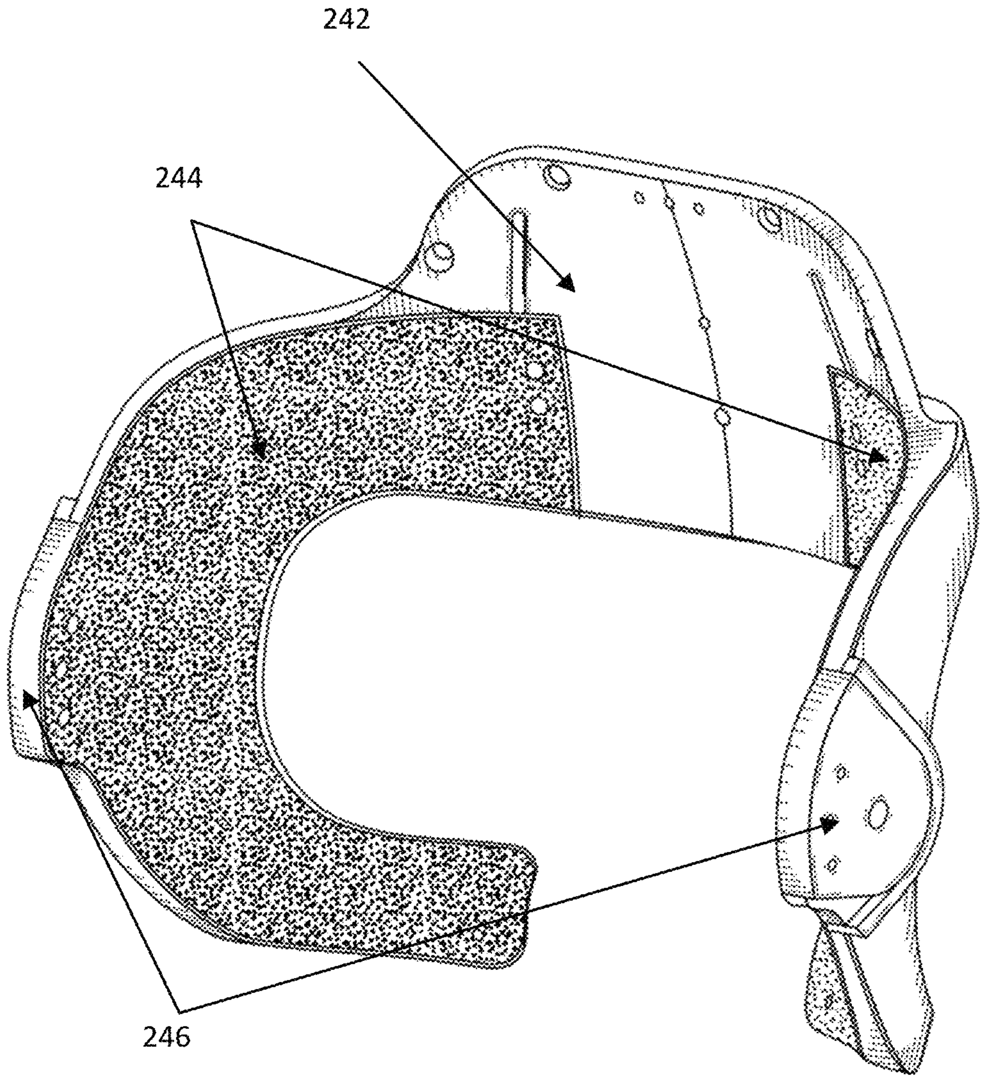
FIG. 2C illustrates an example headgear frame.

For example, FIG. 2C illustrates an example headgear frame 242. A face liner 244 may be attached to the headgear frame 242. The face liner 244 may include a left piece and a right piece. One or more portions of the face liner 244 may be fixed to the headgear frame 242 while one or more other portions of the face 244 may be removably attached/not attached to the headgear frame 242. For example, the portions of the face liner 244 closer to the front of the headgear frame 242 may be fixed to the headgear frame 242, while the rest of the face liner 244 may be removably attached/not attached to the headgear frame 242. Such attachment of the face liner 244 may enable the face liner 244 to be pulled away from the headgear frame 242. For example, the headgear frame 242 may include tabs 246. The tabs 246 may be attached to the face liner 244. The tabs 246 may be moved to change the positioning of the face liner 244 with respect to the headgear frame 242. For example, the tabs 246 may be pulled back to pull the face liner 244 away from the headgear frame 242. In some implementations, the tabs 246 may be connected to one or more headgear tightening mechanisms. For example, the tabs 246 may be connected to headgear tightening mechanism(s) that are controlled via a tightening wheel for the multi-layer headgear system. The user may rotate the tightening wheel to control how tightly the multi-layer headgear system sits on the person's head. Rotation of the tightening wheel may control movement of the tabs 246 to pull the face liner 244 away from the headgear frame 242 or push the face liner 244 into the headgear frame 242.

Figure 2D:
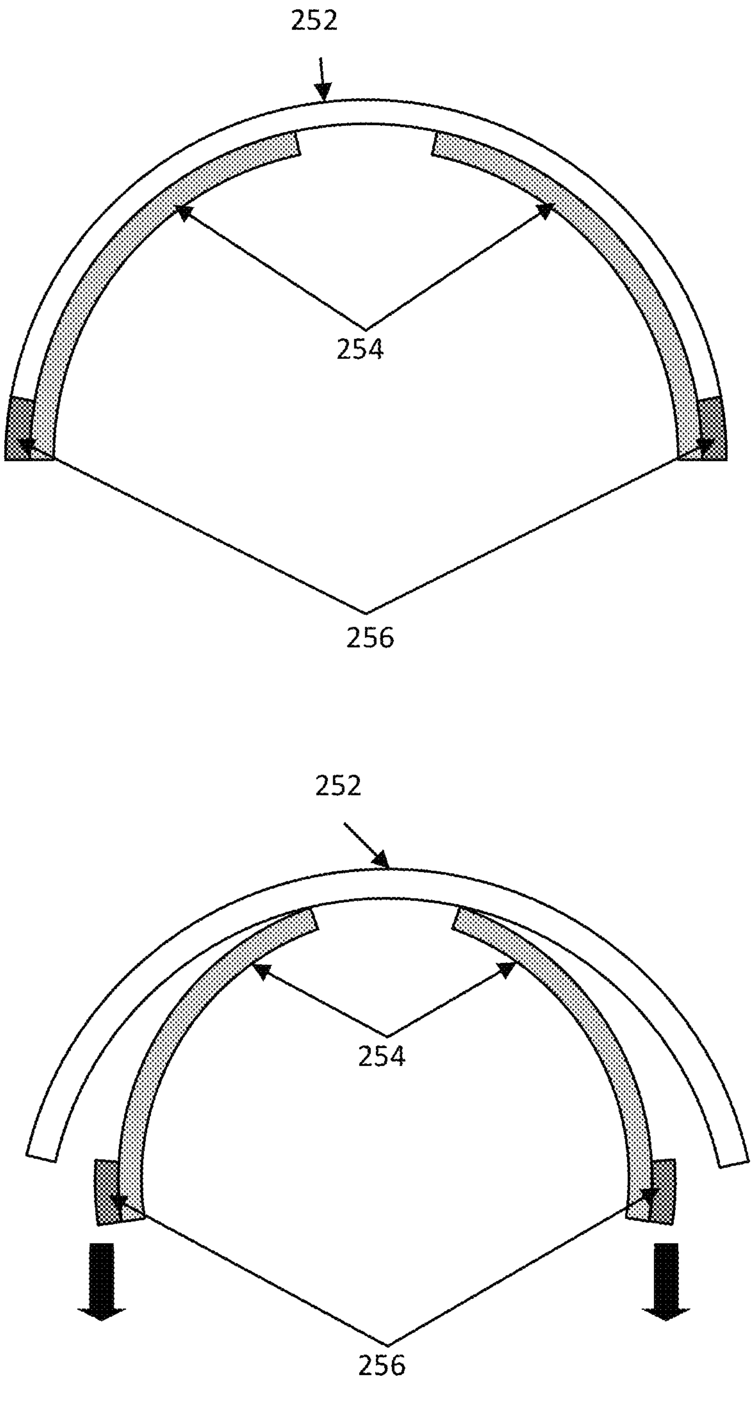
FIG. 2D illustrates an example flexing of a face liner.

FIG. 2D illustrates example change in positioning of a face liner 254 with respect to a headgear frame 252. The face liner 252 may be attached to the headgear frame 252. Sensor(s) and/or foam pad/substrate(s) including sensor(s) may be attached to the face liner 254. Tabs 256 may be attached to the face liner 254. The tabs 256 may be moved to change the positioning of the face liner 254 with respect to the headgear frame 252. For example, the tabs 256 may be pulled back to pull the face liner 254 away from the headgear frame 252. The face liner 254 may be anchored near the front of the headgear frame 252, and pulling the face liner 254 back may squeeze the sensor(s) and/or the foam pad/substrate(s) on the face liner 254 to the face. Other configurations of face liner and headgear frame are contemplated.

Figure 3A:
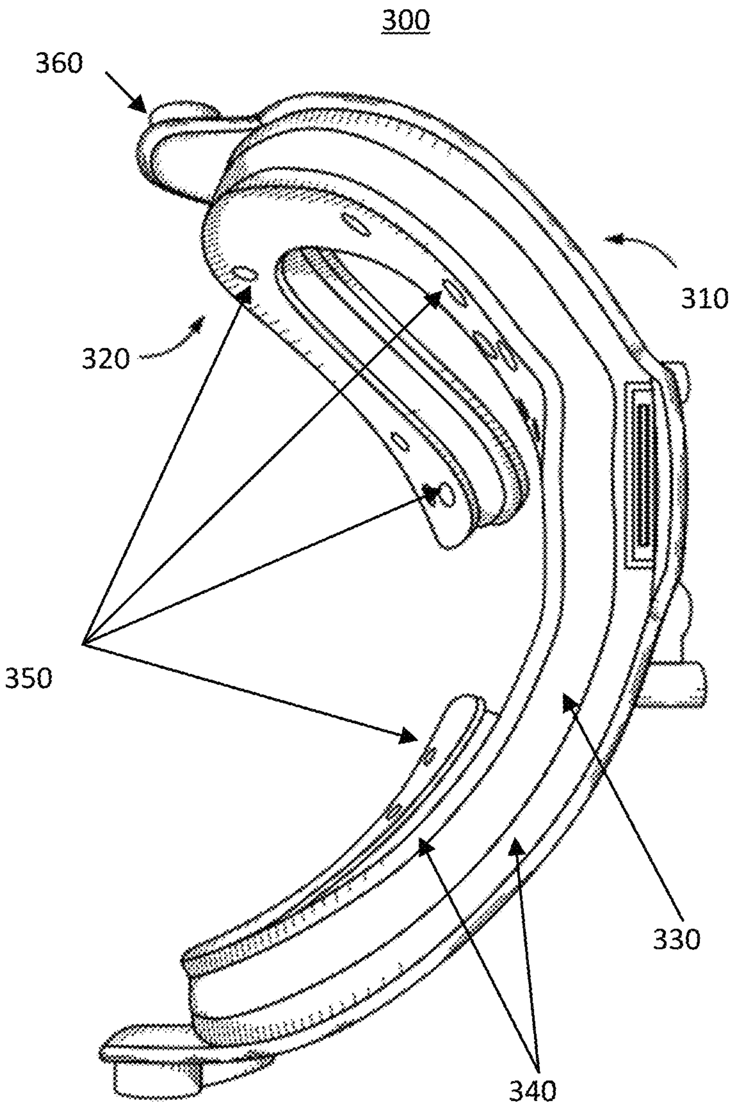
FIGS. 3A and 3B illustrate example views of a sensor-engagement assembly.
Figure 3B:
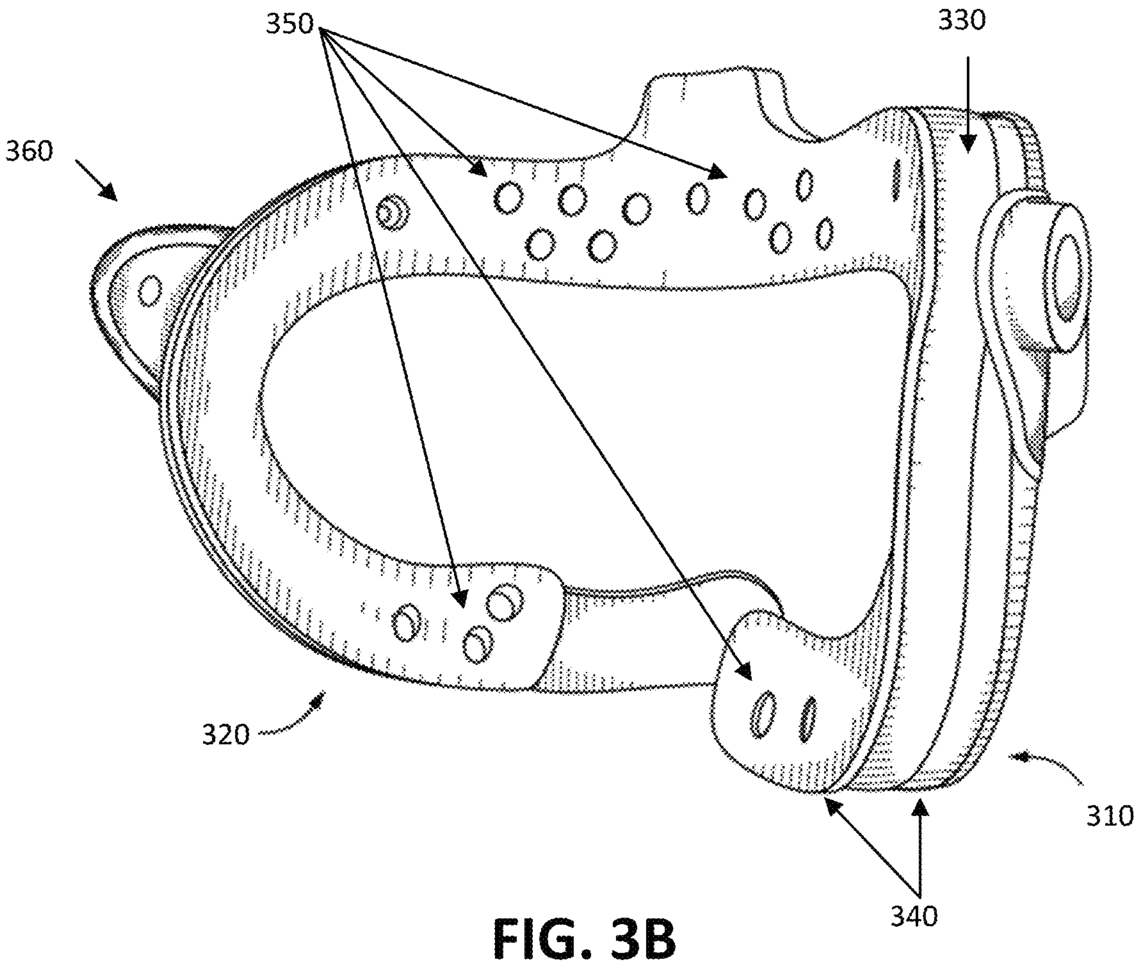

FIGS. 3A and 3B illustrate an example sensor-engagement assembly. FIGS. 3A and 3B provide two views 300, 350 of the sensor-engagement assembly. The sensor-engagement assembly may include a facer liner 310 and a foam pad/substrate 320. The foam pad/substrate 320 may include a compressible layer 330 (e.g., foam) sandwiched by harder layers 340 (e.g., polymeric material, elastic material). Sensors of one or more types may be placed at various locations 350 on the foam pad/substrate 320. The sensors may be removable and replaceable, without needing to disassemble the entire system. Screws may be placed at sides of the facer liner 310 to flex the facer liner 310 and push the foam pad/substrate 320 on a face. Other configuration of sensor-engagement assembly is contemplated.

Figure 4A:
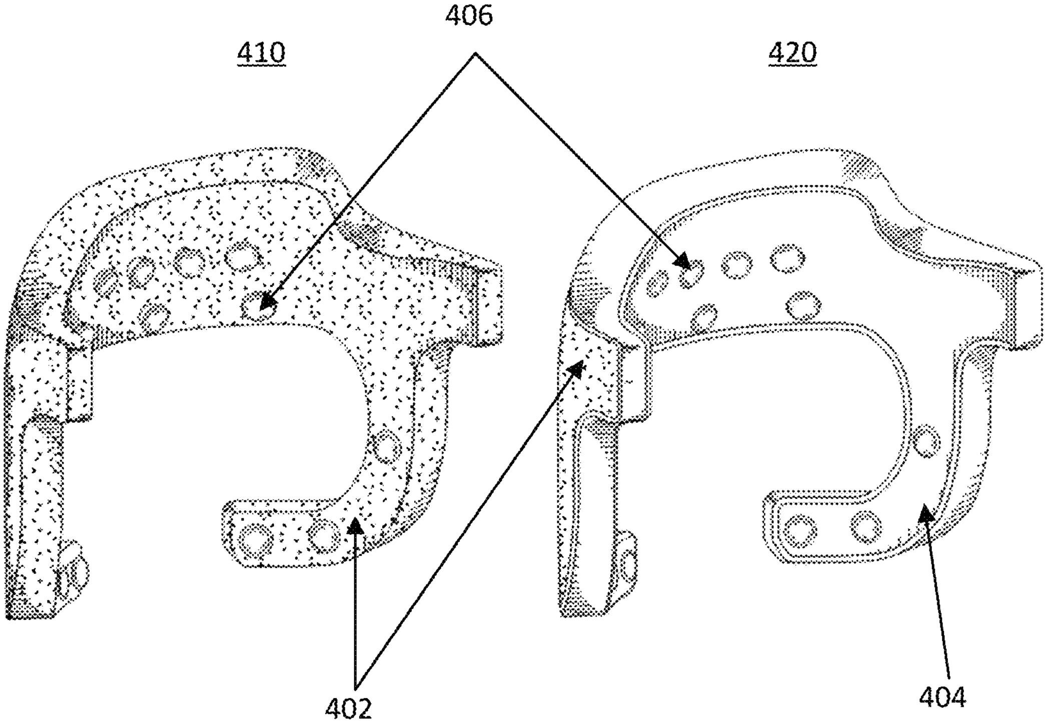
FIG. 4A illustrates an example sensor-engagement assembly.

FIG. 4A illustrates an example sensor-engagement assembly. FIG. 4A provides two views 410, 420 of the sensor-engagement assembly. The sensor-engagement assembly may include a non-removable layer 402 (e.g., non-removable foam pad) and a removable layer 404 (e.g., outer shell). The non-removable layer 402 and the removable layer 404 may have the same material(s)/softness or different material (s)/softness. The combined shape of the non-removable layer 402 and the removable layer 404 may vary in thickness to account for different face shapes and/or sizes. The sensor-engagement assembly may include electrodes 406 in various locations. In some implementations, the electrodes 406 may be removable from the sensor-engagement assembly. For example, an electrode may be a non-removable electrode female piece located within the sensor-engagement assembly and a removable electrode male piece that can be inserted into or removed from the non-removable electrode female piece.

Figure 4B:
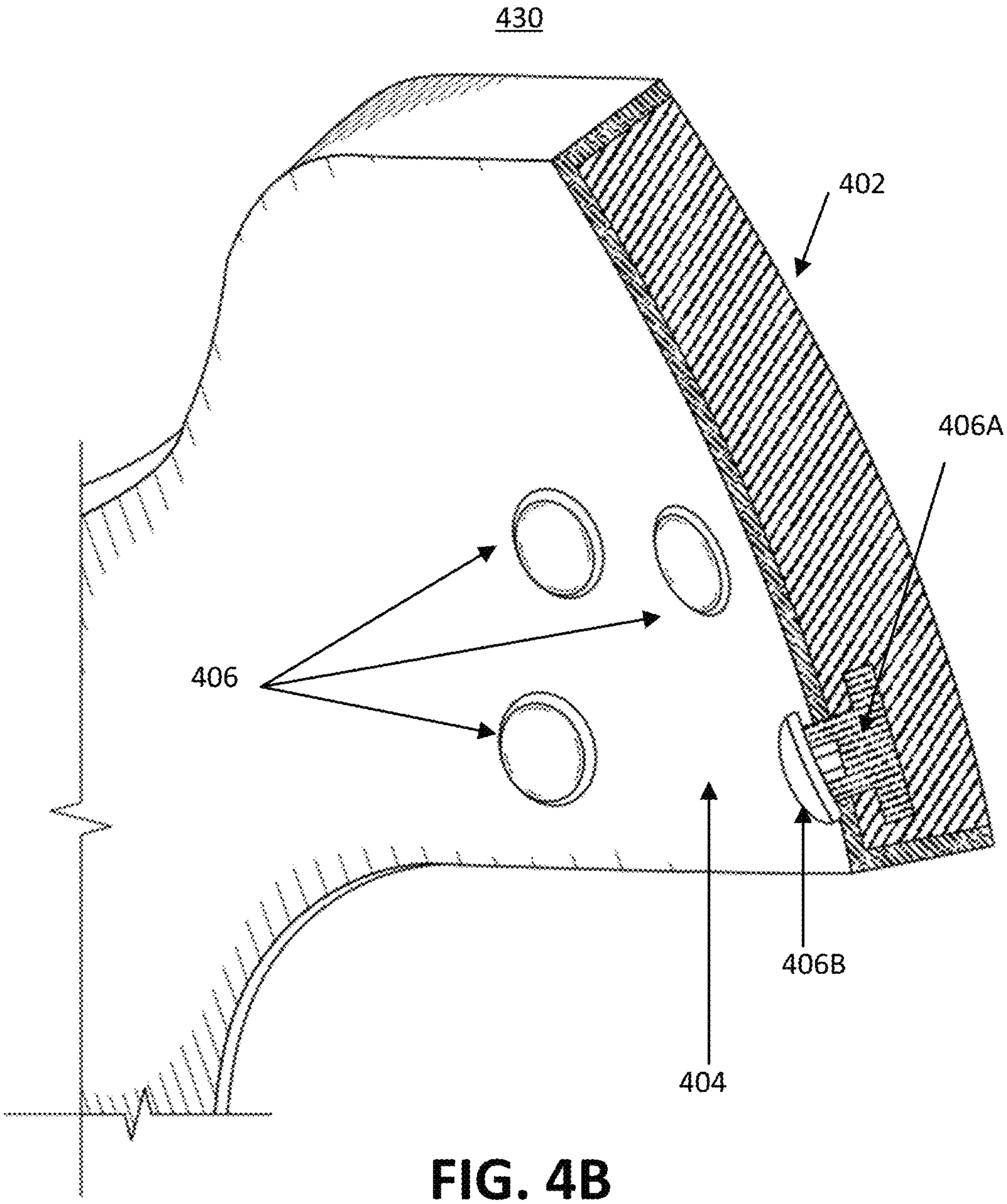
FIG. 4B illustrates an example cross-sectional view of a sensor-engagement assembly.

FIG. 4B illustrates an example cross-sectional view 430 of a sensor-engagement assembly. The sensor-engagement assembly may include a non-removable layer 402 and a removable layer 404. The sensor-engagement assembly may include electrodes 406 in various locations. An electrode may include a non-removable electrode female piece 406A (e.g., non-removable female snap) located within the sensor-engagement assembly and a removable electrode male piece 406B (removable electrode). The removable electrode male piece 406B may be inserted into or removed from the non-removable electrode female piece 406A. The non-removable electrode female piece 406A may be wired to a flexible, or rigid printed circuit board. The printed circuit board may be located on a headgear frame and/or other components of a multi-layer headgear system. For example, the printed circuit board may be located at or near the forehead portion of the headgear frame. Other locations of printed circuit boards are contemplated.

Figure 5:
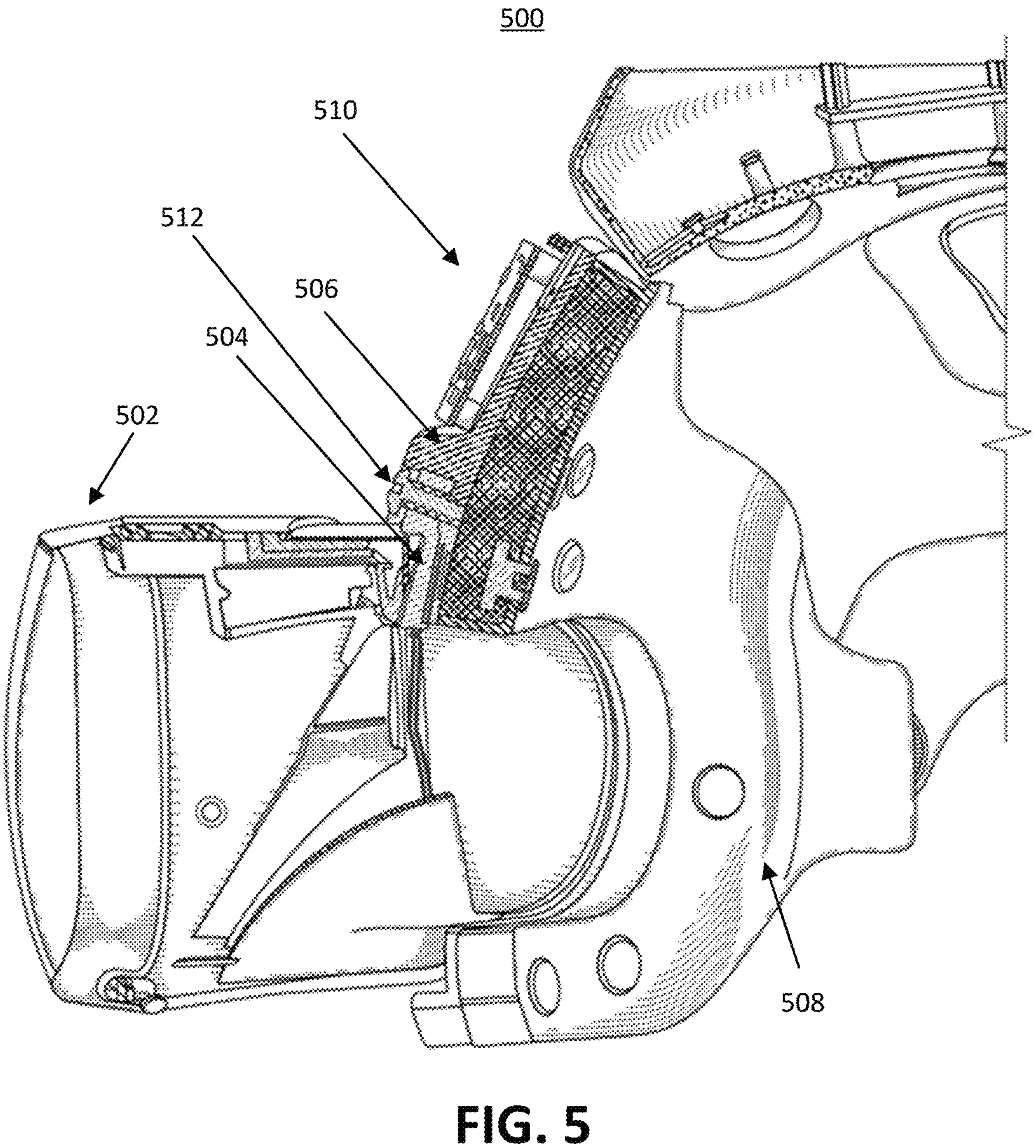
FIG. 5 illustrates an example cross-sectional view of a multi-layer headgear system.

FIG. 5 illustrates an example cross-sectional view 500 of a multi-layer headgear system. The multi-layer headgear system may include a head-mounted display 502, a head-mounted display adapter plate 504, a headgear frame 506, and a sensor-engagement assembly 508. The multi-layer headgear system may include other components, such as a printed circuit board 510. Sensor(s) of the sensor-engagement assembly 508 may be electrically connected to the printed circuit board 510. In some implementations, attachment between the head-mounted display adapter plate 504 and the headgear frame 506 may include one or more screws 512.

Figure 6:
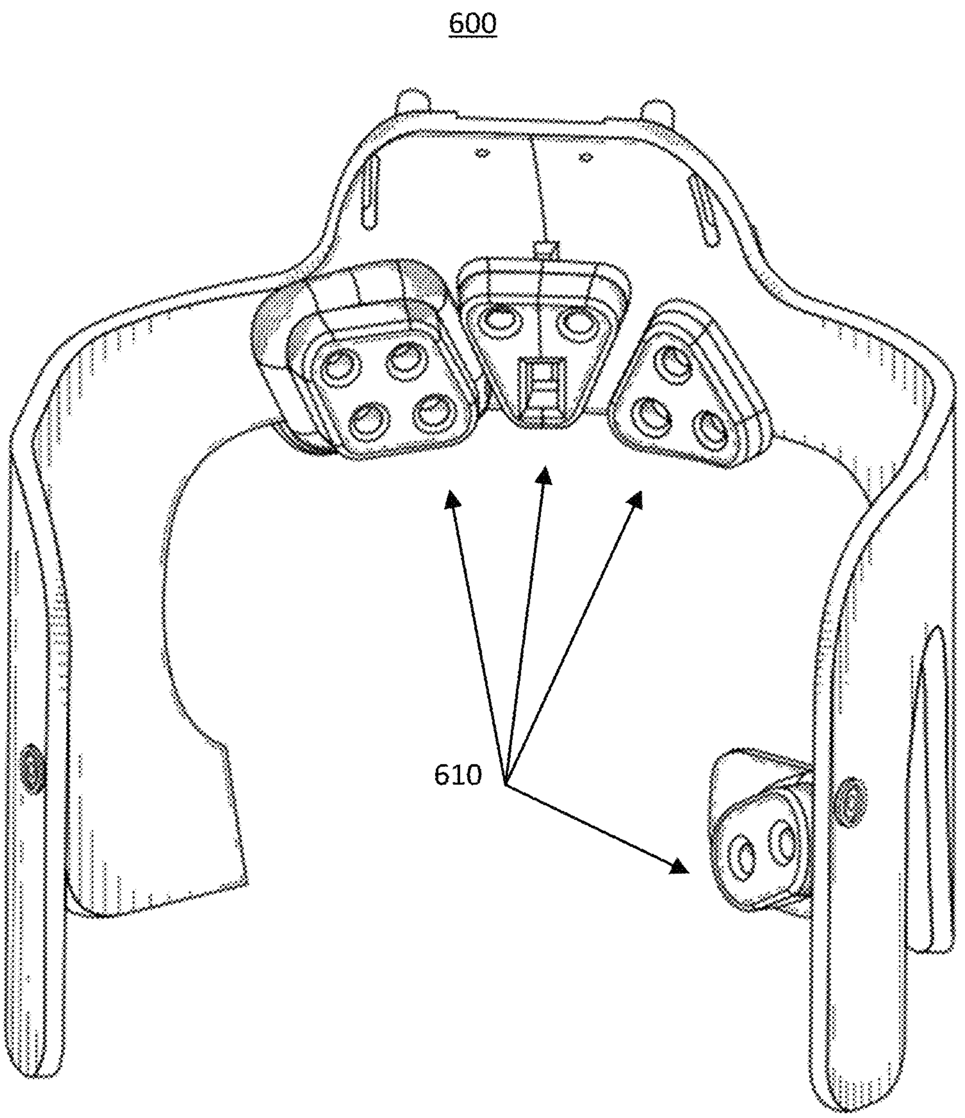
FIG. 6 illustrates an example sensor-engagement assembly.

FIG. 6 illustrates an example sensor-engagement assembly 600. The sensor-engagement assembly 600 may include multiple sensor pad islands 610. The sensor pad islands 610 may include foam pads/substrates, sensors, and/or other components. The sensor pad islands 610 may include the same type or different types of sensors. The sensor pad islands 610 may be attached to various locations in the sensor-engagement assembly 600 to position the sensors at different locations. The sensor pad islands 610 may include one or more compressible layers (e.g., foam). For example, the sensor pad islands 610 may be made of two or more different durometer silicon foam. The sensor pad islands 610 may have custom geometric properties to control comfort and face contact effectiveness.

Figure 7:
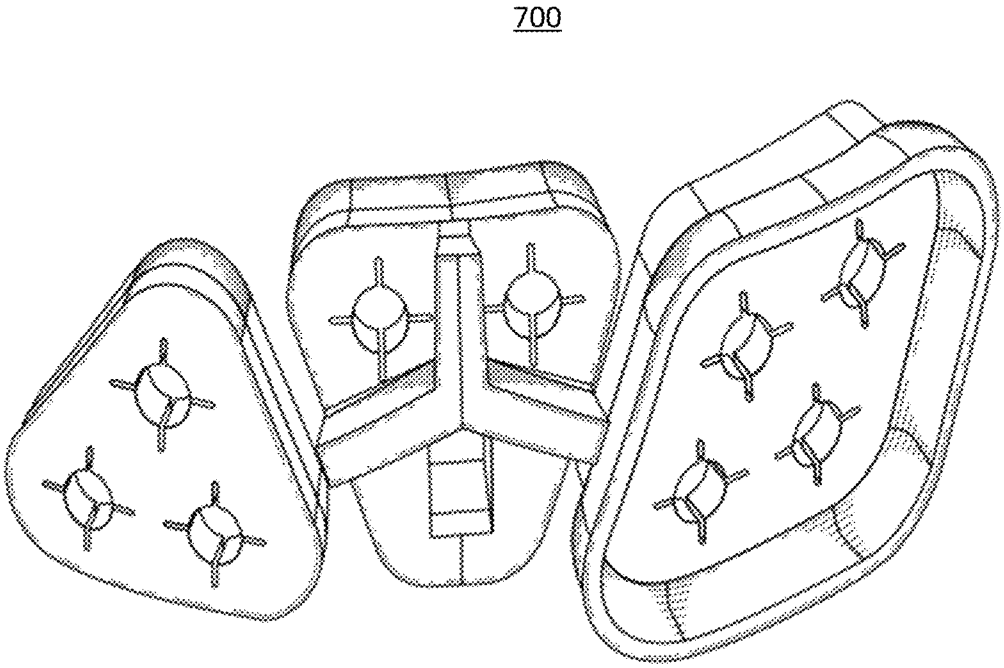
FIG. 7 illustrates example sensor pad islands.

FIG. 7 illustrates example sensor pad islands 700. Three different geometric configurations of sensor pad islands 700 are shown in FIG. 7. FIG. 7 may show the side of the sensor pad islands that are attached to a sensor-engagement assembly. The attachment side of the sensor pad islands 700 may be shaped differently. Different shapes of the sensor pad islands 700 may correspond to different locations of attachment on the sensor-engagement assembly. Other geometric configuration of sensor pad islands is contemplated.

Figure 8A:
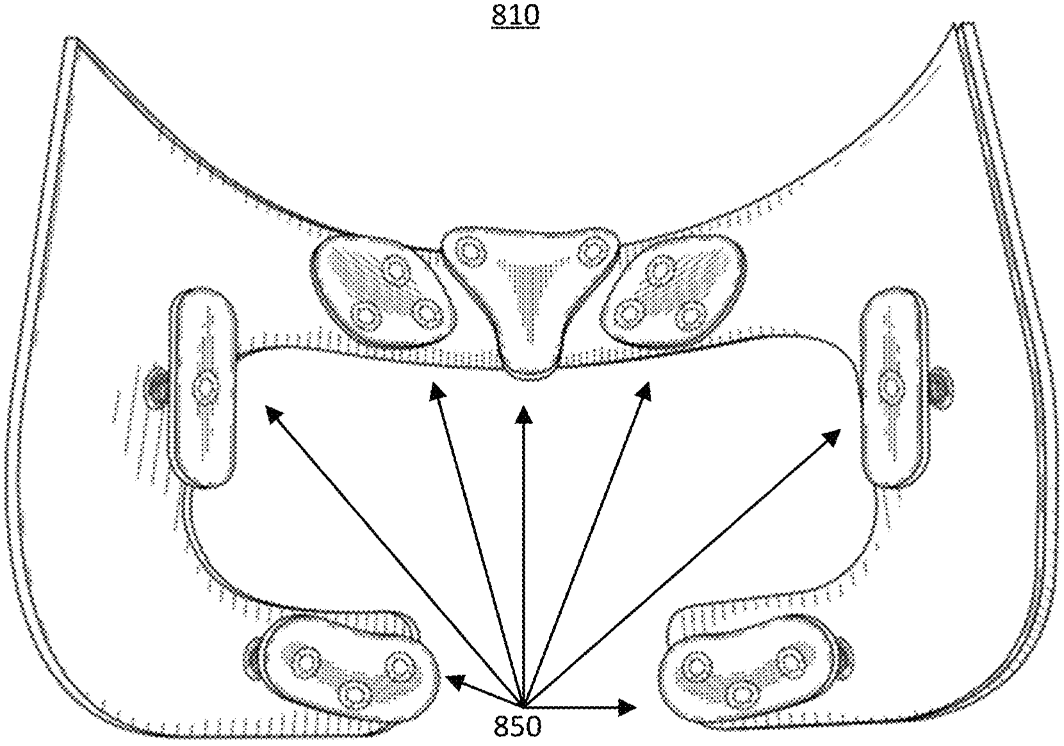
FIGS. 8A, 8B, 8C, and 8D illustrate example views of a sensor-engagement assembly.
Figure 8B:
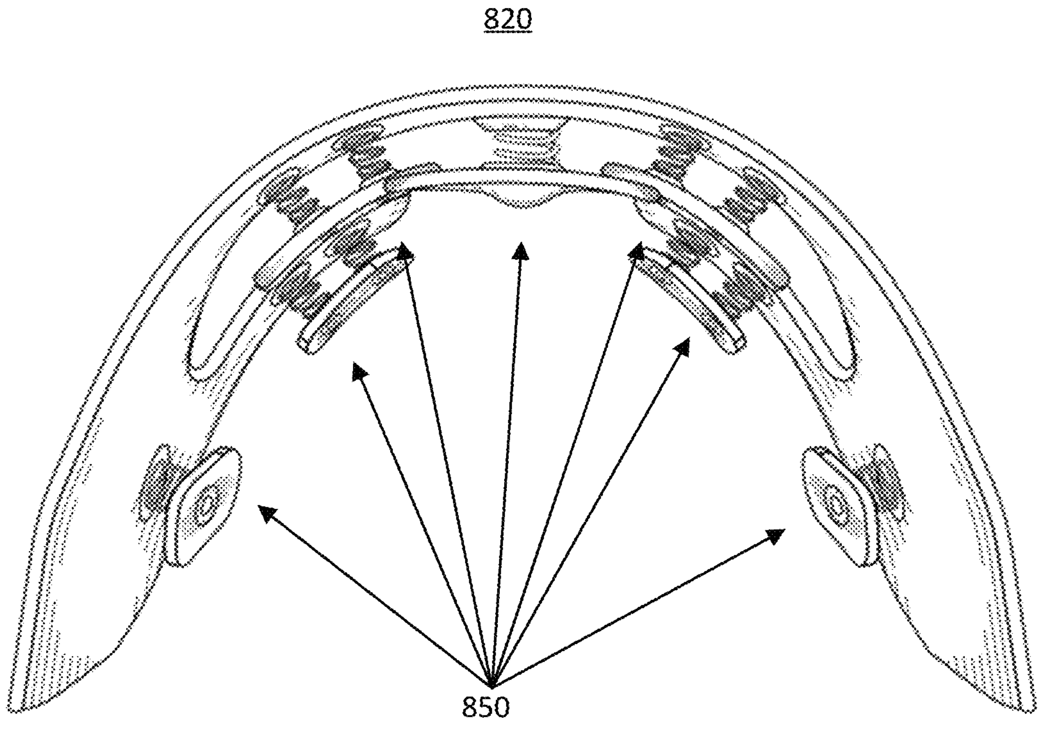
Figure 8C:
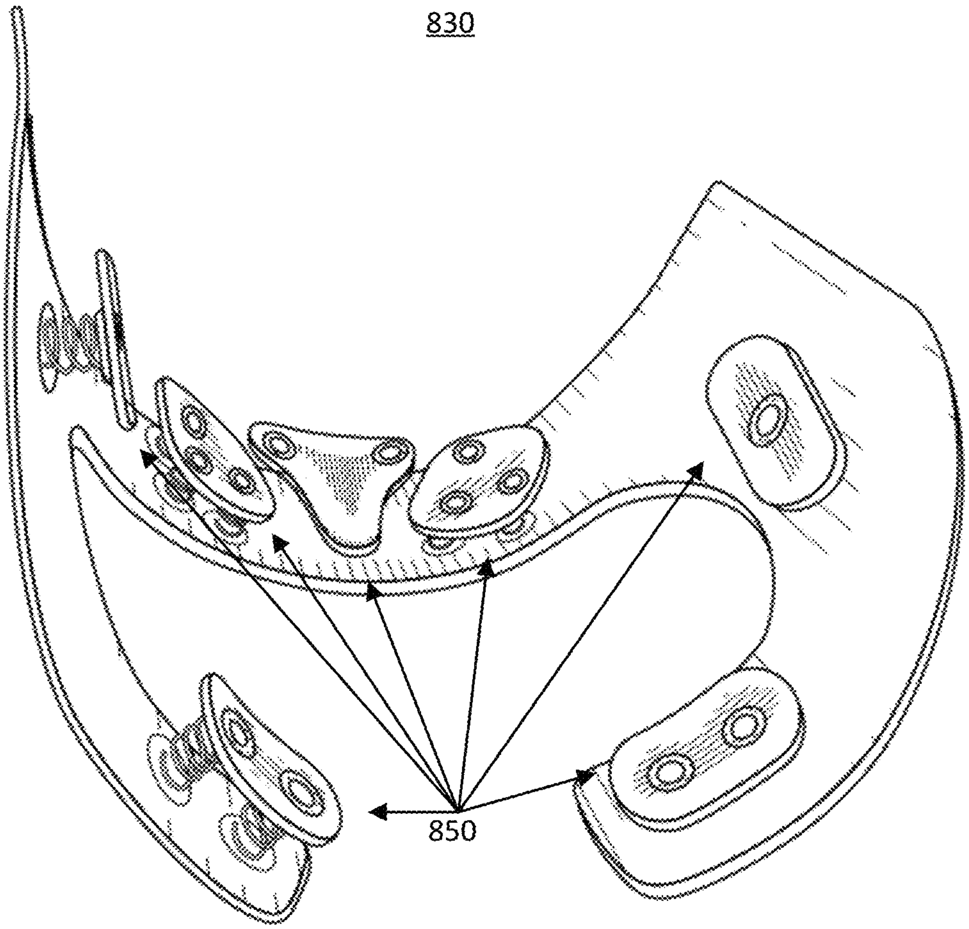
Figure 8D:
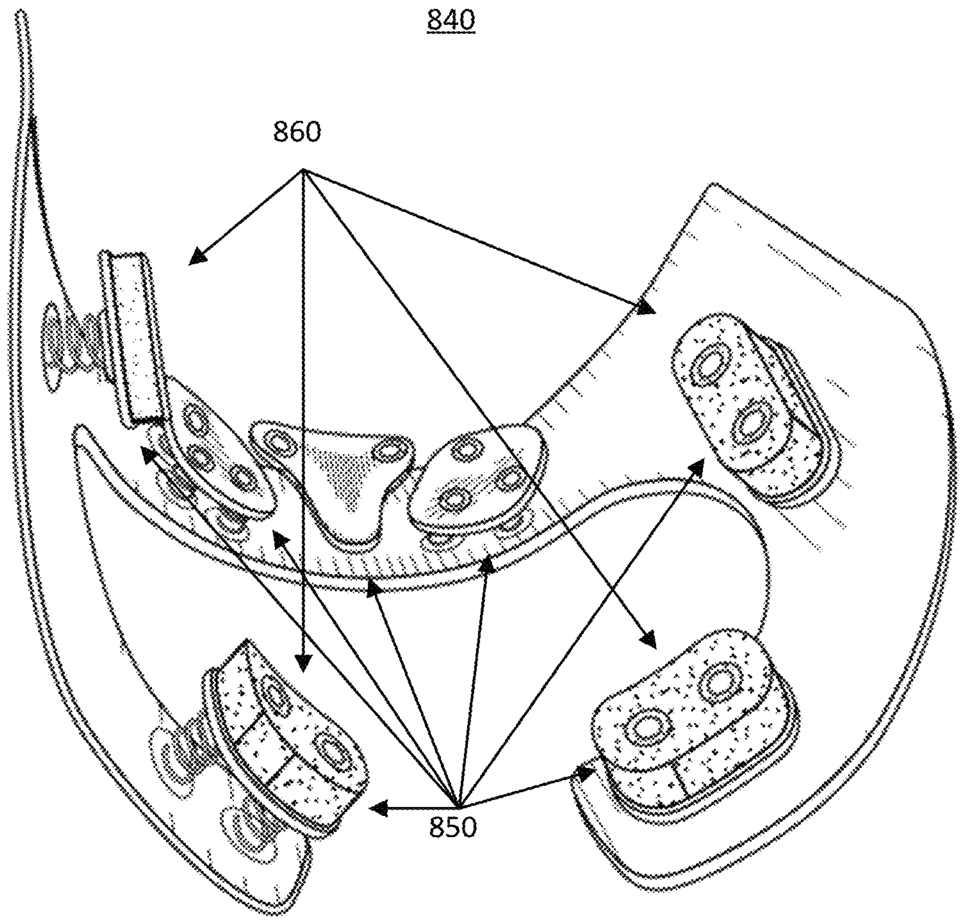

FIGS. 8A, 8B, 8C, and 8D illustrate example views 810, 820, 830, 840 of a sensor-engagement assembly. The sensor-engagement may include various locations (sensor attachment locations) at which sensor pad islands may be attached. Sensor attachment pads 850 may be attached to the sensor-engagement assembly at the sensor attachment locations. Individual sensor attachment pads may be attached to the sensor-engagement assembly via one or more springs. The sensor attachment pads may be marked with symbols/ images to represent where the sensors/electrodes will be located when sensor islands are attached to the sensor attachment pads. The view 840 in FIG. 8D shows example placement of four sensor islands 860 on the sensor attachment pads 850.

In some implementations, the head-mounted display adapter plate may be configured to be removably attached to the headgear frame. For example, the backside of the head-mounted display adapter plate may be configured to be removably attached to the frontside of the headgear frame. The head-mounted display adapter plate being removably attached to the headgear frame include the head-mounted display adapter plate being attached to the headgear frame so that the head-mounted display adapter plate can be removed/detached from the headgear frame. The head-mounted display adapter plate may be removed/detached from the headgear frame to remove the head-mounted display, which is attached to the head-mounted display adapter plate, from the multi-layer headgear system.

Figure 9A:
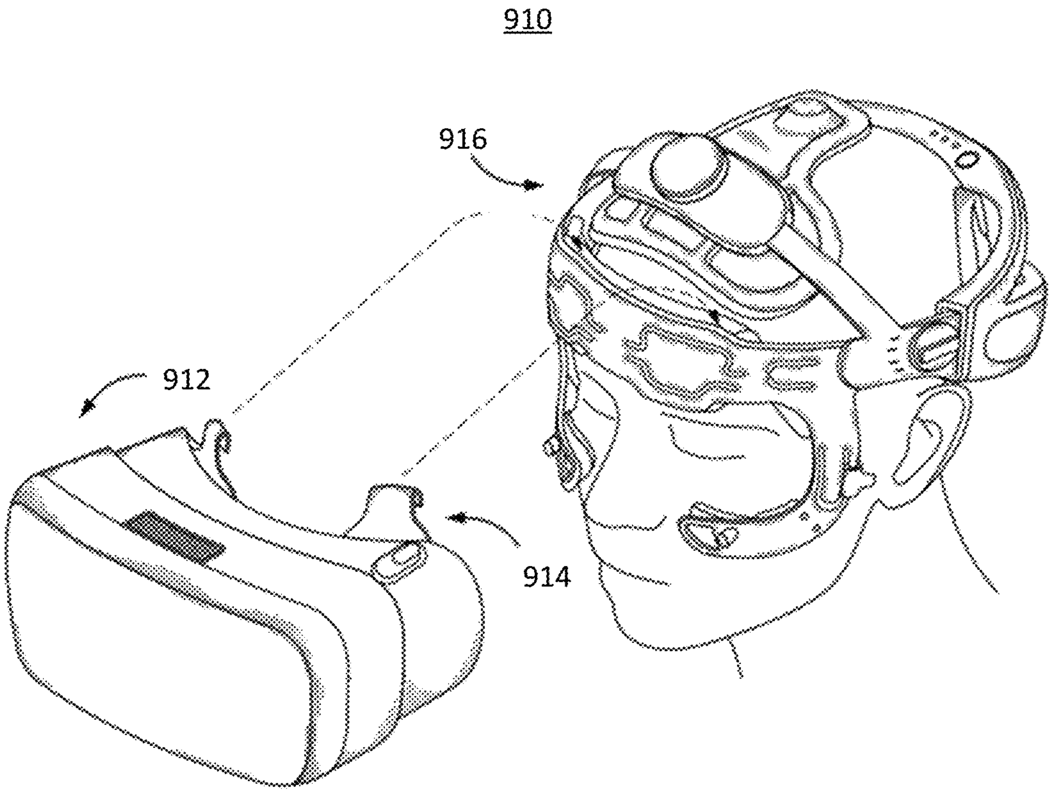
FIGS. 9A, 9B, 9C, 9D, 9E, 9F, and 9G illustrate example multi-layer headgear systems.

FIGS. 9A, 9B, 9C, 9D, 9E, 9F, and 9G illustrate example multi-layer headgear systems 910, 920, 930, 940, 950, 960, 970 in which a head-mounted display adapter plate is removably attached to a headgear frame. In FIG. 9A, a head-mounted display 912 may be attached to a head-mounted display adapter plate 914. The head-mounted display adapter plate 914 may be removably attached to a headgear frame 916. The head-mounted display adapter plate 914 may include on the top hooks that attach to the top portion of the headgear frame 916. For example, the top hooks of the head-mounted display adapter plate 914 may clip over the top portion of the headgear frame 916. The head-mounted display adapter plate 914 may include magnets and/or snapping posts that attach to the bottom portion of the headgear frame 916. The headgear frame 916 may include one or more buttons to release the head-mounted display adapter plate 914 from the headgear frame 916.

Figure 9B:
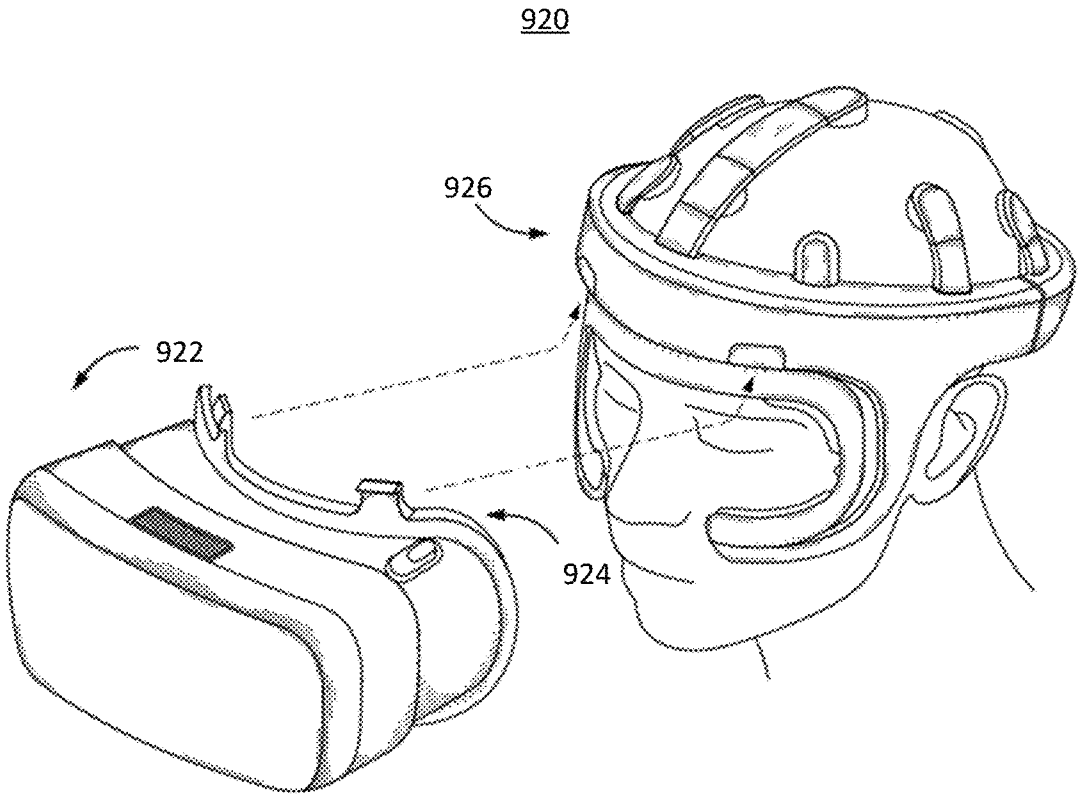

In FIG. 9B, a head-mounted display 922 may be attached to a head-mounted display adapter plate 924. The head-mounted display adapter plate 924 may be removably attached to a headgear frame 926. The head-mounted display adapter plate 924 may include on the top hooks that attach to (e.g., clip onto) the top portion of the headgear frame 926. For example, the top hooks of the head-mounted display adapter plate 924 may clip under the top portion of the headgear frame 926. The head-mounted display adapter plate 924 may include magnets and/or snapping posts that attach to the bottom portion of the headgear frame 926. The headgear frame 926 may include one or more buttons to release the head-mounted display adapter plate 924 from the headgear frame 926.

Figure 9C:
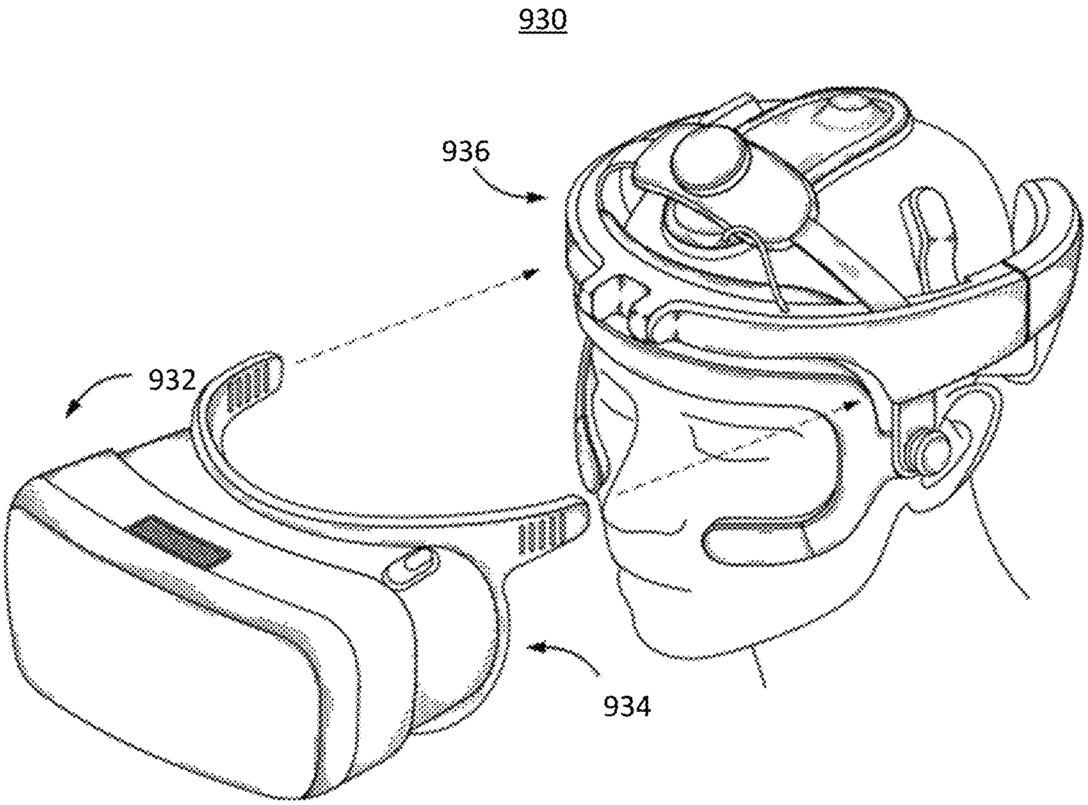

In FIG. 9C, a head-mounted display 932 may be attached to a head-mounted display adapter plate 934. The head-mounted display adapter plate 934 may be removably attached to a headgear frame 936. The head-mounted display adapter plate 934 may include indexing arms that can be pushed into the headgear frame 936. The indexing arms may be held onto place on the headgear frame 936 via friction. The user may overcome this friction and pull the head-mounted display adapter plate 934 off the headgear frame 936. The strength of the attachment may be controlled by friction fit, springs, and/or other material characteristics.

Figure 9D:
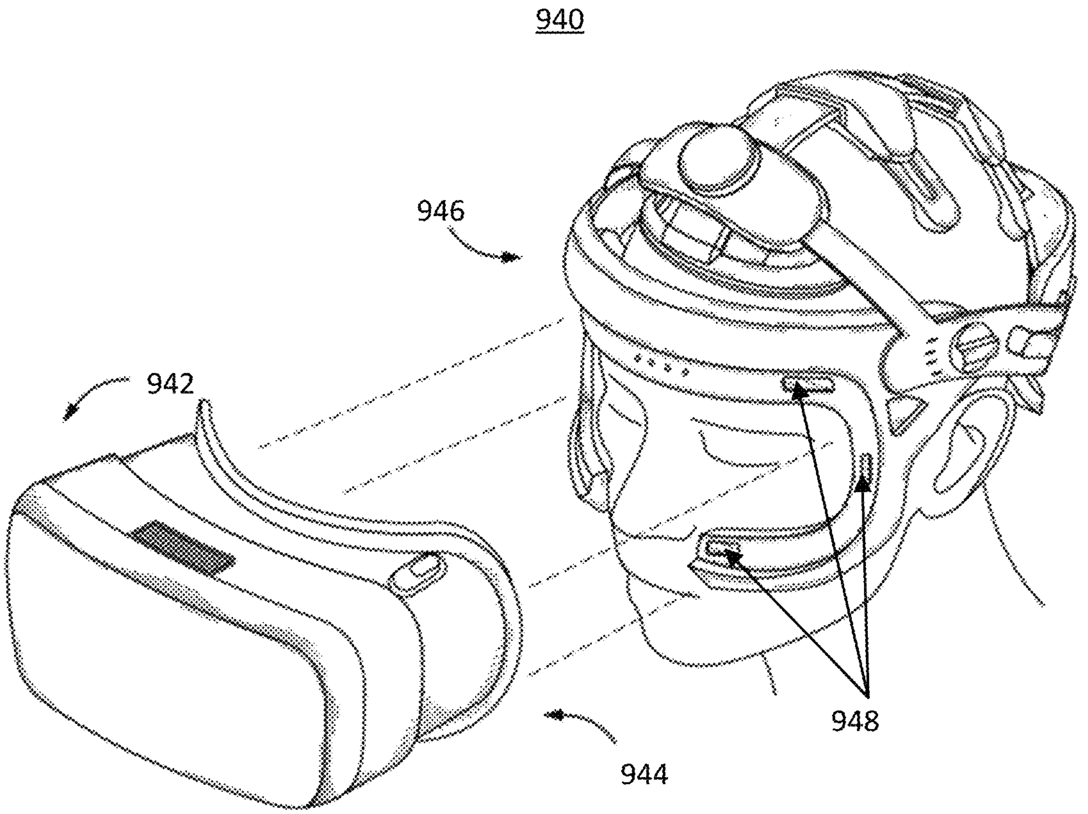

In FIG. 9D, a head-mounted display 942 may be attached to a head-mounted display adapter plate 944. The head-mounted display adapter plate 944 may be removably attached to a headgear frame 946. The head-mounted display adapter plate 944 and/or the headgear frame 946 may include magnetic materials 948 to attach the head-mounted display adapter plate 944 to the headgear frame 946. For example, magnets may be placed on both the head-mounted display adapter plate 944 and the headgear frame 946. As another example, magnets may be placed on the head-mounted display adapter plate 944 and ferromagnetic metals may be placed on the headgear frame 946, or vice versa. The magnetic materials may be mounted to be inset from the rest of the head-mounted display adapter plate 944/the headgear frame 946.

Figure 9E:
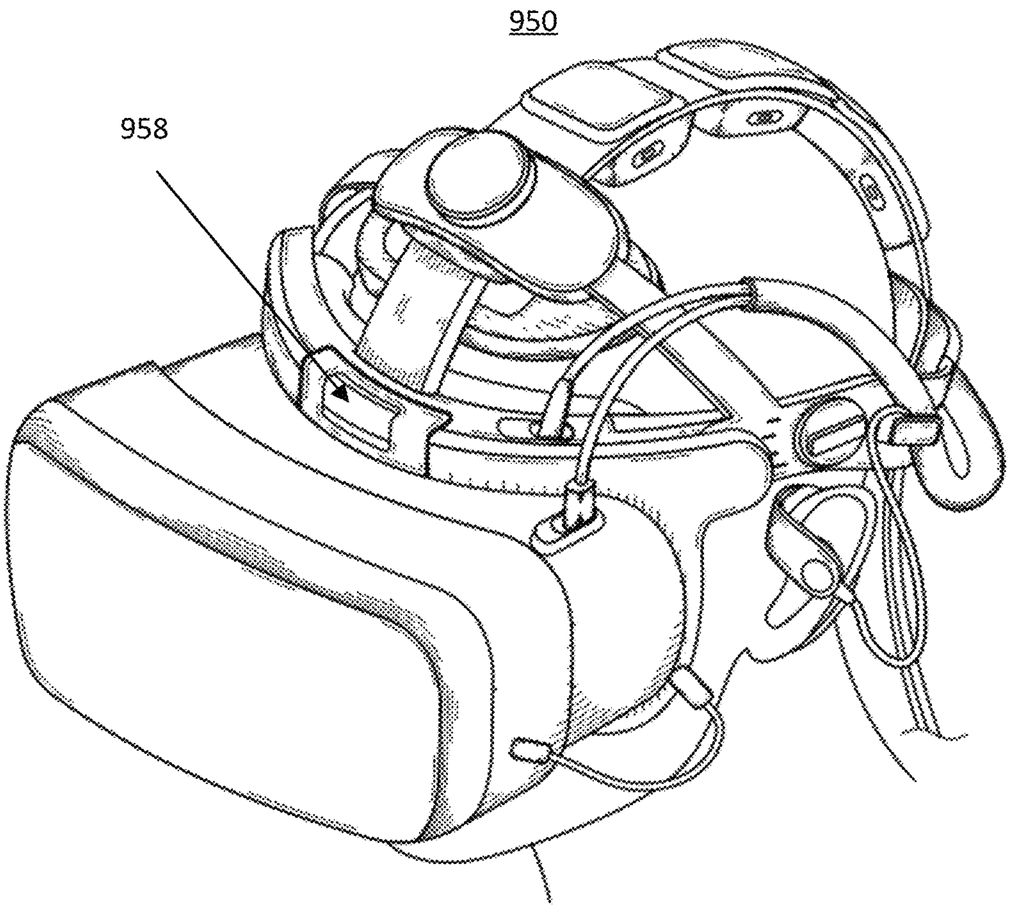

In FIG. 9E, a head-mounted display may be attached to a head-mounted display adapter plate, and the head-mounted display adapter plate may be removably attached to a headgear frame. A button mechanism 958 may be used to lock the head-mounted display adapter plate on the headgear frame. The button mechanism 958 may be used to release the head-mounted display adapter plate from the headgear frame.

Figure 9F:
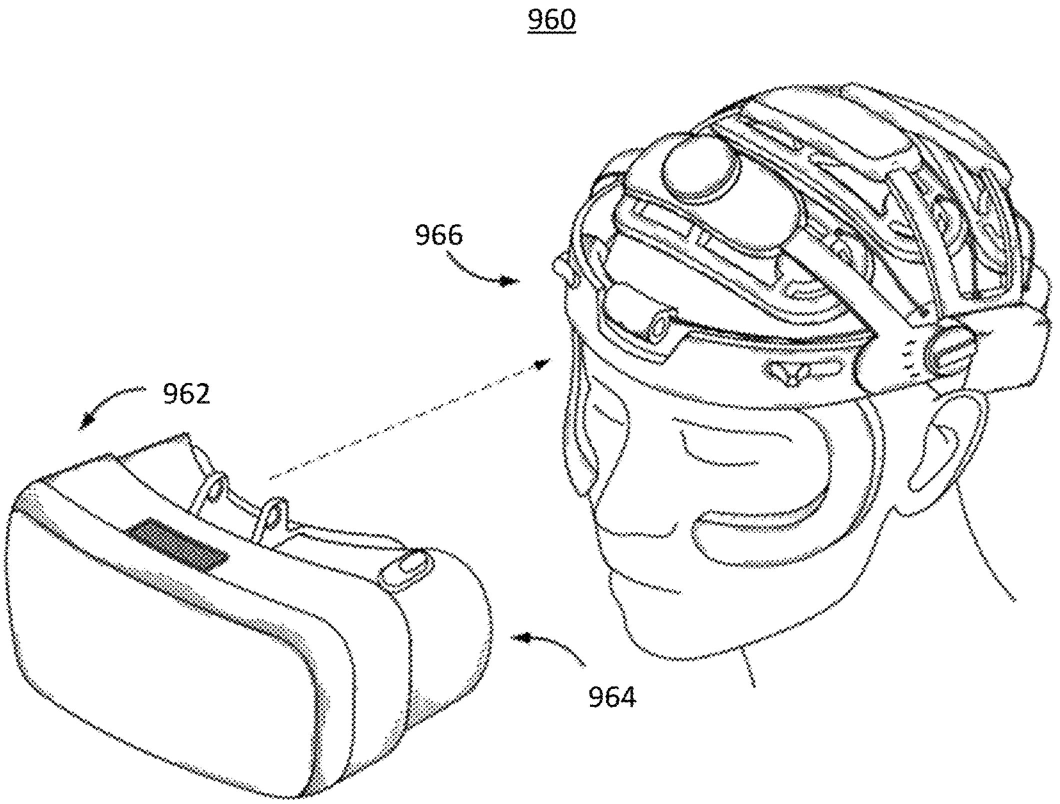
Figure 9G:
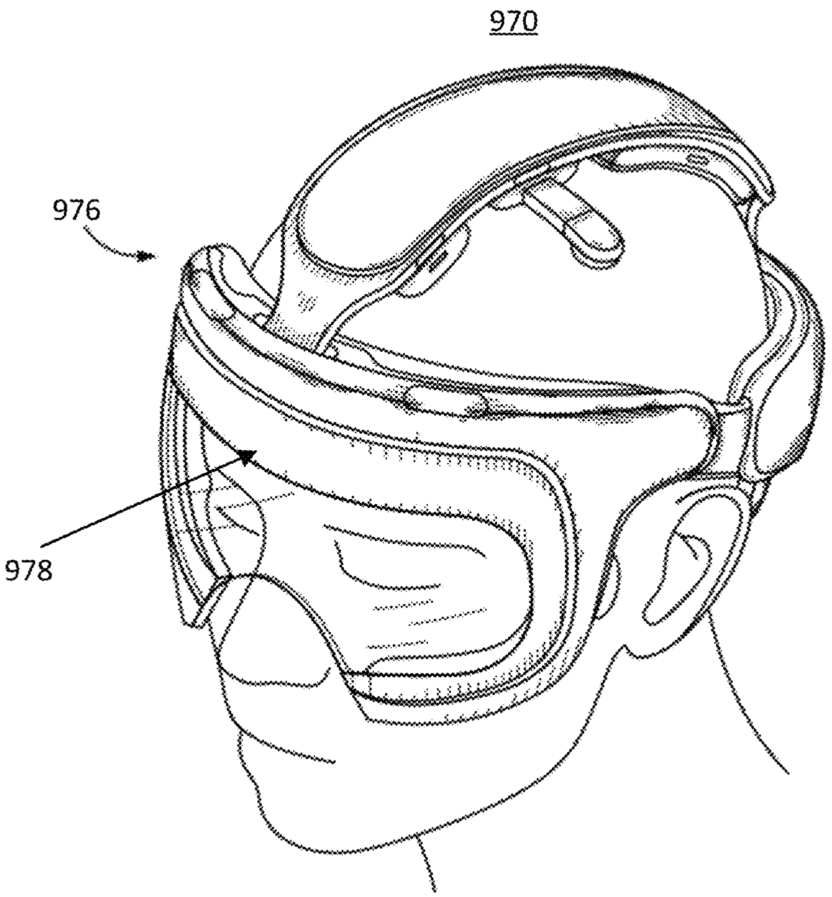

In FIG. 9F, a head-mounted display 962 may be attached to a head-mounted display adapter plate 964. The head-mounted display adapter plate 964 may be removably attached to a headgear frame 966. The head-mounted display adapter plate 964 and the headgear frame 966 may include complimentary hinges. The hinges may be attached using a pin (e.g., a clevis pin). The pin may include a spring-loaded locking mechanism to keep it in the hinge unless it is forcibly removed from the hinge. The pin may be removed to detach the head-mounted display adapter plate 964 from the headgear frame 966. The hinge(s) may include a locking mechanism to hold the head-mounted display adapter plate 964 and the head-mounted display in upright position. The hinge(s) may include friction to hold the head-mounted display adapter plate 964 and the head-mounted display in upright position.

Use of the hinge to attach the head-mounted display adapter plate 964 to the headgear frame 966 may enable the head-mounted display adapter plate 964 to be rotated with respect to the headgear frame 966. Other removable attachment of the head-mounted display adapter plate to the headgear frame is contemplated.

In some implementations, the headgear frame may be weighted to be balanced when the head-mounted display adapter plate and the head-mounted display are attached to the headgear frame. For example, the back portion of the headgear frame may weigh more than the front portion of the headgear frame to offset the weight imbalance when the head-mounted display adapter plate and the head-mounted display are attached to the headgear frame. Without the head-mounted display adapter plate and the head-mounted display, the headgear frame may be unbalanced.

When the head-mounted display adapter plate and the head-mounted display are not attached to the headgear frame, a counterbalance plate may be attached to the headgear frame. For example, in FIG. 9G, a counterbalance plate 978 may be attached to a headgear frame 976. The counterbalance plate may provide substituted weight for the head-mounted display adapter plate and the head-mounted display. The counterbalance plate may be attached to the headgear frame via screws, fasteners, clips, magnets, fittings, snaps, and/or other attachment techniques/tools. The counterbalance plate may include one or more lenses, one or more polymeric substrates, and/or one or more metal counterweights. In some implementations, the lens may be a fully mechanical lens (e.g., clear polymeric lens) or an electronic display. The electronic display may be connected electrically through pins on the front of the headgear frame.

In some implementations, the head-mounted display adapter plate may be configured to be rotatably attached to the headgear frame. For example, the backside of the head-mounted display adapter plate may be configured to be rotatably attached to the frontside of the headgear frame. The head-mounted display adapter plate being rotatably attached to the headgear frame include the head-mounted display adapter plate being attached to the headgear frame so that the head-mounted display adapter plate can be rotated with respect to the headgear frame (e.g., flipped up and down). The head-mounted display adapter plate may be rotated with respect to the headgear frame to rotate the head-mounted display, which is attached to the head-mounted display adapter plate, out of sight of the person using the multi-layer headgear system.

In some implementations, the head-mounted display adapter plate may be configured to be locked with the headgear frame. For example, the backside of the head-mounted display adapter plate may be configured to be locked with the frontside of the headgear frame. When the head-mounted display adapter plate is rotated/flipped down, the head-mounted display adapter plate may be locked in place with the headgear frame via screws, fasteners, clips, magnets, fittings, snaps, and/or other attachment techniques/tools. Such locking of the head-mounted display adapter plate to the headgear frame may keep the head-mounted display in position during use. For example, the user may look down without the head-mounted display rotating away due to gravity.

Figure 10A:
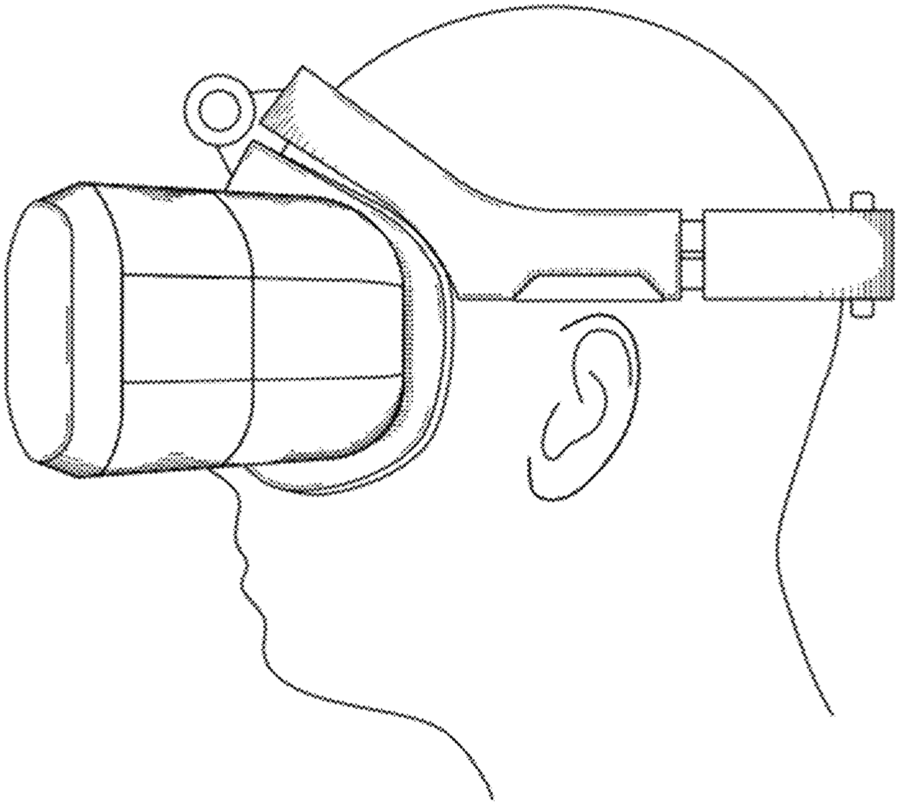
Figure 10B:
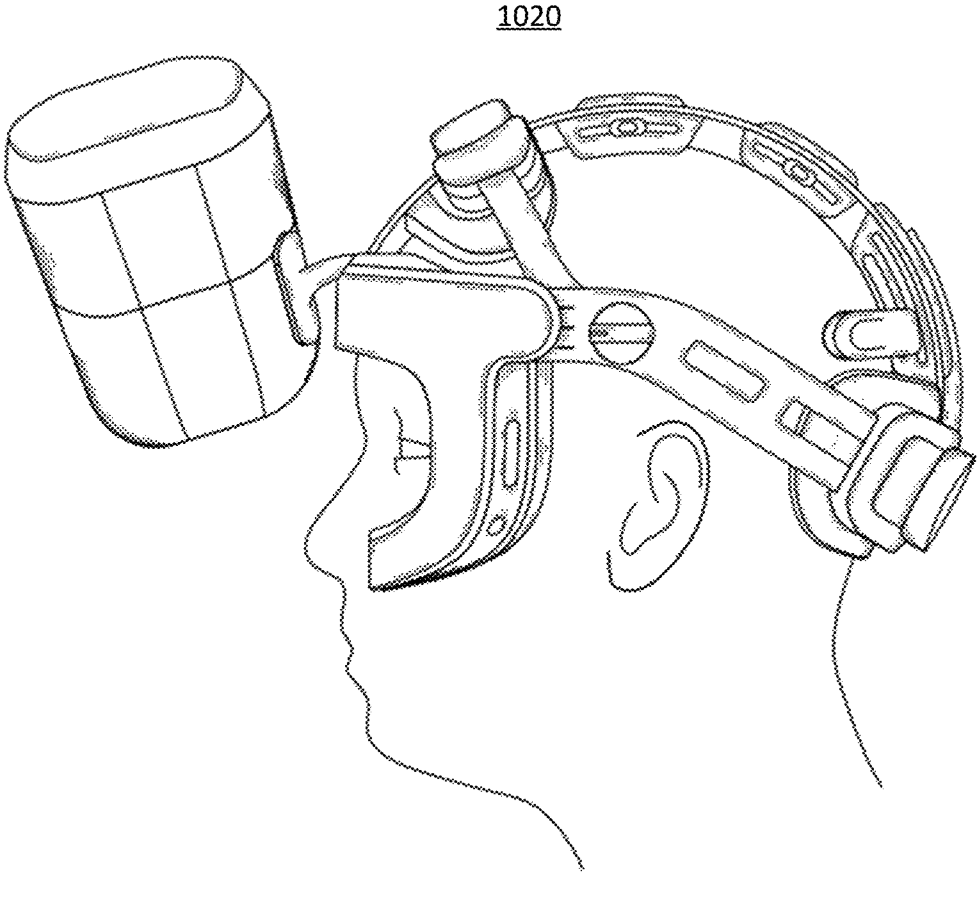
Figure 10C:
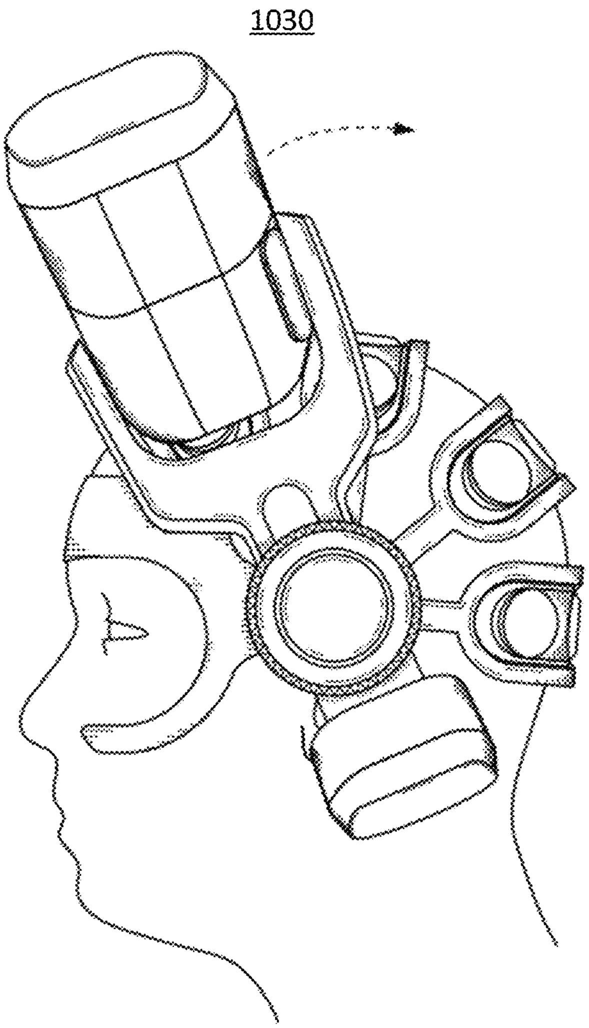

FIGS. 10A, 10B, and 10C illustrate example multi-layer headgear systems 1010, 1020, 1030 in which a head-mounted display adapter plate is rotatable attached to a headgear frame. In FIG. 10A, a head-mounted display adapter plate is rotatable attached to a headgear frame via hinges on the head-mounted display adapter plate and the headgear frame. The hinges may be joined together using a pin (e.g., a clevis pin). In FIG. 10B, a head-mounted display adapter plate is rotatable attached to a headgear frame. The head-mounted display adapter plate may be rotated away from the user's face, which also moves the head-mounted display out of the user's line of sight. Rotating the head-mounted display adapter plate out of the user's line of sight may enable the user to look around without removing the multi-layer headgear system 1020 from the head. In FIG. 10C, the head-mounted display adapter plate may be rotated around an axis that goes through the user's head. The head-mounted display adapter plate and the head-mounted display may be swiveled on the bearing located on the sides of the headgear frame so that the front of the user's face is entirely open. A counterweight may be placed on the back-side of the rotating arm to head the head-mounted display adapter plate and the head-mounted display stationary at different positions. The rotating arm may have indexes to notify the user on whether the head-mounted display adapter plate and the head-mounted display are out of the way or in a locked position. Other rotatable attachment of the head-mounted display adapter plate to the headgear frame is contemplated.

Figure 11:
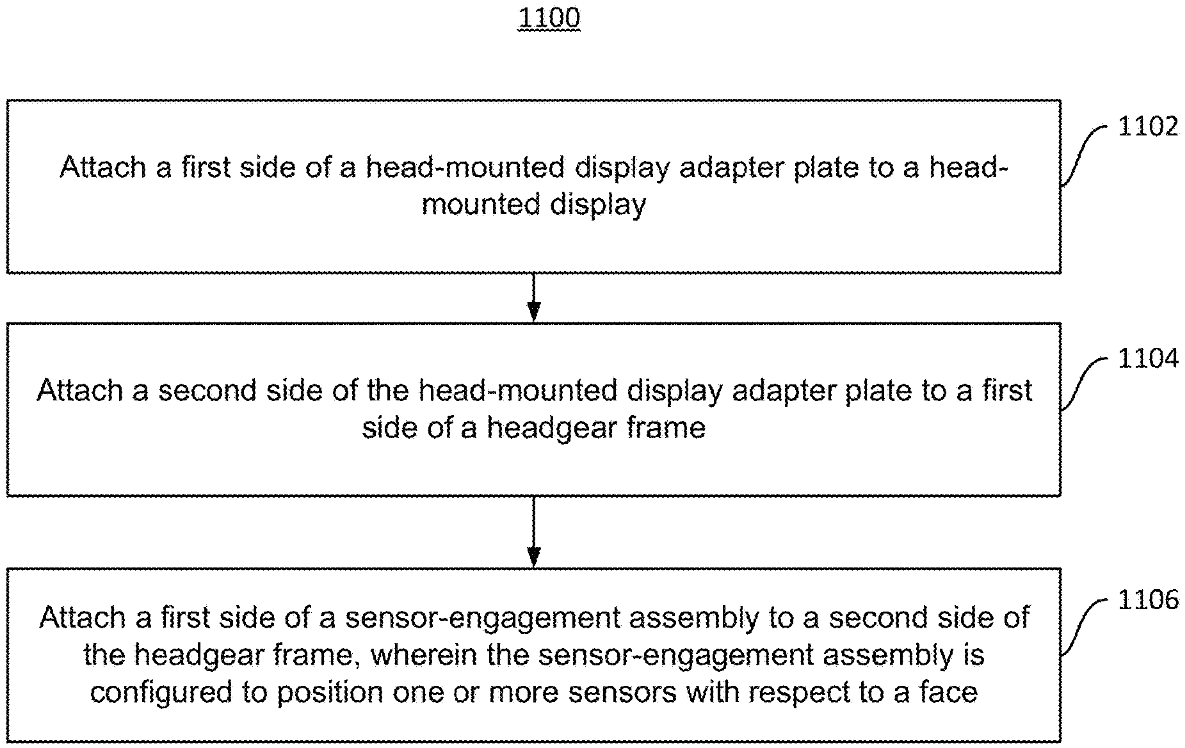
FIG. 11 illustrates an example method for utilizing a multi-layer headgear system.

FIG. 11 illustrates method 1100 for utilizing a multi-layer headgear system. The operations of method 1100 presented below are intended to be illustrative. In some implementations, method 1100 may be accomplished with one or more additional operations not described, and/or without one or more of the operations discussed. In some implementations, two or more of the operations may occur substantially simultaneously.

At operation 1102, a first side of a head-mounted display adapter plate may be attached to a head-mounted display.

At operation 1104, a second side of the head-mounted display adapter plate may be attached to a first side of a headgear frame.

At operation 1106, a first side of a sensor-engagement assembly may be attached to a second side of the headgear frame. The sensor-engagement assembly may be configured to position one or more sensors with respect to a face.

Although the head-mounted display 102, the head-mounted display adapter plate 104, the headgear frame 106, and the sensor-engagement assembly 108 are shown in FIG. 1 as single entities, this is for illustrative purposes only. One or more of the components of the system 100 may be contained within a single device or across multiple devices.

While the disclosure has been described above using different figures, one or more features/functionalities described with respect to one figure is not limited to the one figure and may be applied to other aspects of the disclosure. For example, one or more features/functionalities described with respect to FIG. 1 may be applied to other aspects of the disclosure (e.g., as described with respect to other figures).

Although the system(s) and/or method(s) of this disclosure have been described in detail for the purpose of illustration based on what is currently considered to be the most practical and preferred implementations, it is to be understood that such detail is solely for that purpose and that the disclosure is not limited to the disclosed implementations, but, on the contrary, is intended to cover modifications and equivalent arrangements that are within the spirit and scope of the appended claims. For example, it is to be understood that the present disclosure contemplates that, to the extent possible, one or more features of any implementation can be combined with one or more features of any other implementation.

What is claimed is:

1. A multi-layer headgear system, comprising:
a headgear frame; and
a sensor-engagement assembly attached to the headgear frame comprising:
one or more biometric sensors configured to measure one or more biometric characteristics; and
a face liner carrying the one or more biometric sensors, the face liner being configured to bias the one or more biometric sensors toward one or more targeted locations on a face of a person in an as-used mode upon the headgear frame being worn by the person.

2. The multi-layer headgear system of claim 1, wherein the face liner is made of flexible material.

3. The multi-layer headgear system of claim 1, wherein:
the face liner is configured to be flexed onto the face; and
responsive to the face liner being flexed onto the face, the face liner conforms to a shape of the face.

4. The multi-layer headgear system of claim 3, wherein compressive or mechanical pressure is applied on the face liner to bias the one or more biometric sensors toward the one or more targeted locations.

5. The multi-layer headgear system of claim 1, wherein:
one or more foam pads or one or more substrates are attached to the face liner; and
the one or more foam pads or the one or more substrates include the one or more biometric sensors.

6. The multi-layer headgear system of claim 1, wherein the face liner is a single-piece face liner.

7. The multi-layer headgear system of claim 1, wherein the face liner is a multi-piece face liner.

8. The multi-layer headgear system of claim 7, wherein the multi-piece face liner includes a left piece for a left side of the face and a right piece for a right side of the face.

9. The multi-layer headgear system of claim 1, wherein the face liner includes a first portion fixed to the headgear frame and a second portion not attached directly to the headgear frame.

10. The multi-layer headgear system of claim 1, wherein the face liner includes a first portion fixed to the headgear frame and a second portion removably attached to the headgear frame.

11. A method for utilizing a multi-layer headgear system, the multi-layer headgear system comprising a headgear frame, a sensor-engagement assembly attached to the headgear frame, one or more biometric sensors configured to measure one or more biometric characteristics, and a face liner carrying the one or more biometric sensors, the face liner being configured to bias the one or more biometric sensors toward one or more targeted locations on a face of a person in an as-used mode upon the headgear frame being worn by the person, the method comprising:

positioning the headgear frame on a head; and manipulating the sensor-engagement assembly to bias the one or more biometric sensors toward the one or more targeted locations on the face.

12. The method of claim 11, wherein the face liner is made of flexible material.

13. The method of claim 11, wherein:

the face liner is configured to be flexed onto the face; and responsive to the face liner being flexed onto the face, the face liner conforms to a shape of the face.

14. The method of claim 13, wherein compressive or mechanical pressure is applied on the face liner to bias the one or more biometric sensors toward the one or more targeted locations.

15. The method of claim 11, wherein:

one or more foam pads or one or more substrates are attached to the face liner; and the one or more foam pads or the one or more substrates include the one or more biometric sensors.

16. The method of claim 11, wherein the face liner is a single-piece face liner.

17. The method of claim 11, wherein the face liner is a multi-piece face liner.

18. The method of claim 17, wherein the multi-piece face liner includes a left piece for a left side of the face and a right piece for a right side of the face.

19. The method of claim 11, wherein the face liner includes a first portion fixed to the headgear frame and a second portion not directly attached to the headgear frame.

20. The method of claim 11, wherein the face liner includes a first portion fixed to the headgear frame and a second portion removably attached to the headgear frame.

* * * * *